United States Patent [19]

Lahm

[11] Patent Number: 5,006,524

[45] Date of Patent: Apr. 9, 1991

[54] TRIPHENYL PYRAZOLINE COMPOUNDS WHICH ARE USEFUL AS INSECTICIDES

[75] Inventor: George P. Lahm, Wilmington, Del.

[73] Assignee: E. I. Du Pont de Nemours and Company, Wilmington, Del.

[21] Appl. No.: 438,467

[22] PCT Filed: Jul. 15, 1988

[86] PCT No.: PCT/US88/02335

§ 371 Date: Jan. 2, 1990

§ 102(e) Date: Jan. 2, 1990

[87] PCT Pub. No.: WO89/00562

PCT Pub. Date: Jan. 26, 1989

Related U.S. Application Data

[63] Continuation-in-part of Ser. No. 74,795, Jul. 17, 1987, abandoned.

[51] Int. Cl.$^5$ .................. A01N 43/56; C07D 231/06

[52] U.S. Cl. .................. 514/232.2; 514/236.5; 514/316; 514/326; 514/406; 544/82; 544/140; 546/187; 546/211; 548/379

[58] Field of Search .................. 544/140, 82; 546/187, 546/208, 211; 548/379; 514/226, 316, 326, 232.2, 236.5, 406

[56] References Cited

U.S. PATENT DOCUMENTS 4,156,007 5/1979 van Daalen et al. ............... 548/379

FOREIGN PATENT DOCUMENTS 0058424 8/1982 European Pat. Off. ............ 548/379
0153127 8/1985 European Pat. Off. ............ 548/379

Primary Examiner—Robert Gerstl
Assistant Examiner—Zinna Northington-Davis
Attorney, Agent, or Firm—James A. Costello

[57] ABSTRACT

Triphenylpyrazoline compounds, including all of their geometric isomers, stereoisomers and agriculturally suitable salts; agricultural compositions containing them; and use of such compounds as insecticides.

15 Claims, No Drawings

TRIPHENYL PYRAZOLINE COMPOUNDS WHICH ARE USEFUL AS INSECTICIDES

CROSS-REFERENCE TO RELATED APPLICATION

This application is a continuation-in-part of the application bearing U.S. Ser. No. 74,795 filed on July 17, 1987, now abandoned.

BACKGROUND OF THE INVENTION

The described triphenylpyrazolines and agricultural compositions containing them are useful as insecticides.

EPA 21,506 discloses insecticidal compounds of the formula

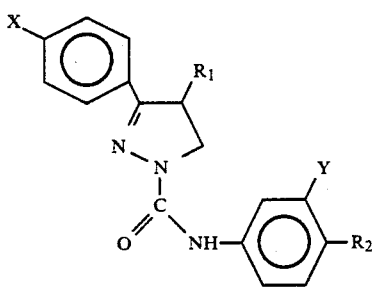

wherein

R$_1$ is a phenyl group;

R$_2$ is a halogenalkoxy, halogenalkenyloxy, halogenalkylthio, halogenalkenylthio, halogenalkylsulfonyl or halogenalkenylsulfonyl group having 1 to 6 carbon atoms; and X and Y represent hydrogen or halogen.

EPA 65,334 discloses insecticidal compounds of the formula

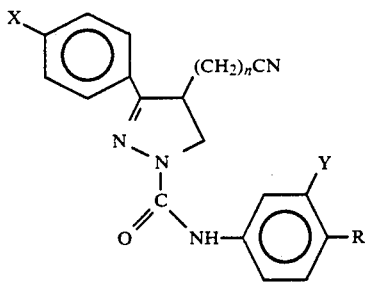

wherein

R is alkoxycarbonyl;

X and Y are hydrogen or halogen, and n is 2, 3, or 4.

EPA 58,424 discloses insecticidal compounds of the formula

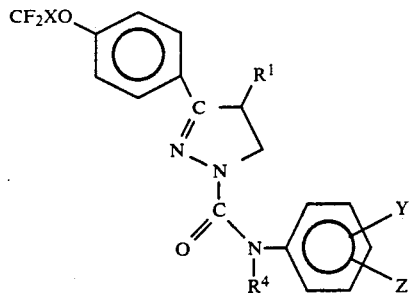

wherein

R$^1$ is phenyl;

R$^4$ is hydrogen or lower alkyl;

X is hydrogen or halogen;

Y and Z are hydrogen, halogen, lower alkyl, lower alkoxy, nitro, trifluoromethyl, lower alkylthio, acyl, nitrile, lower alkylsulfonyl, lower alkoxycarbonyl, A-R$^5$ or Y and Z form

A is O, S, SO, or SO$_2$ and R$^5$ is halogensubstituted lower alkyl.

EPA 113,213 discloses insecticidal compounds of the formula

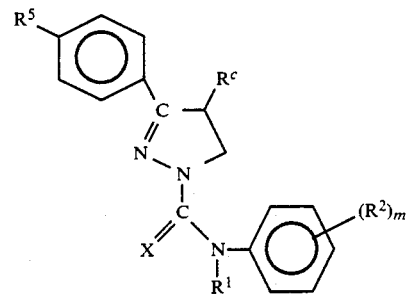

wherein

R$^1$ is hydrogen, alkyl or alkenyl;

X is oxygen or sulfur;

R$^2$ is halogen, alkyl, haloalkyl, cyano, nitro, alkoxy, haloalkoxy, alkylthio, haloalkylthio, alkylsulfonyloxy, alkylsulfonyl, alkoxycarbonyl or acyl, or two adjacent R$^2$ groups may form a ring;

m is 0 to 4;

R$^c$ is phenyl, para substituted by R$_4$;

R$^4$ and R$^5$ are R$^8$SO$_2$O, hydrogen, halogen, alkyl, haloalkoxy, alkylthio or alkylsulfonyl, wherein R$^8$ is alkyl or haloalkyl; at least one of R$^4$ and R$^5$ is R$^8$SO$_2$O, or R$^4$ is haloalkoxy.

EPA 153,127 discloses insecticidal compounds of the formula

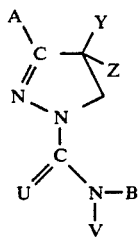

wherein

A and B are phenyl or substituted phenyl;

U is O or S;

V is hydrogen, cycloalkyl, aryl or $R^4$-Q;

Y is unsubstituted or substituted alkyl, unsubstituted or substituted aryl; and

Z is cycloalkyl, unsubstituted or substituted aryl or $R^4$-Q Provided that Z is not hydrogen and Z is not methyl when Y is methyl; and $R^4$-Q is broadly defined.

U.S. Pat. No. 4,156,007 discloses insecticidal compounds of the formula

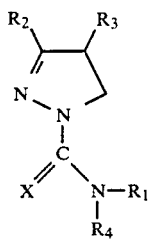

wherein $R_1$ is phenyl or substituted phenyl;

$R_2$ and $R_3$ are equal or different and have the meanings of an alkyl group, a cycloalkyl group, a pyridyl or thienyl group which may be substituted with halogen, alkyl or nitro, a phenyl group or a phenyl group substituted with 1-2 substituents selected from the group consisting of a halogen atom, an alkyl group possibly substituted with halogen, a cycloalkyl group, an alkylthio group, an alkoxy group, a mono or dialkylamino group, a nitro group, a phenyl group possibly substituted with halogen, and a cyano group;

$R_4$ is hydrogen or alkyl; and

X is oxygen or sulfur.

SUMMARY OF THE INVENTION

This invention pertains to compounds of Formula I, including all geometric and stereoisomers, agriculturally suitable salts thereof, agricultural compositions containing them and their use as insecticides:

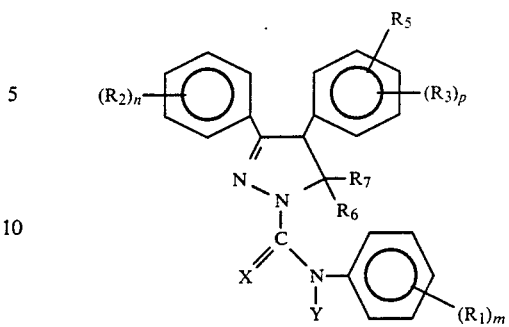

wherein $R_1$, $R_2$ and $R_3$ are independently selected from $R_8$, halogen, CN, $N_3$, SCN, $NO_2$, $OR_8$, $SR_8$, $S(O)R_8$, $S(O)_2R_8$, $OC(O)R_8$, $OS(O)_2R_8$, $C(O)OR_8$, $C(O)R_8$, $C(O)NR_8R_9$, $S(O)_2NR_8R_9$, $NR_8R_9$, $NR_9C(O)R_8$, $OC(O)NHR_8$, $NR_9C(O)NHR_8$ and $NR_9S(O)_2R_8$, or when m, n or p is 2, $R_1$, $R_2$ or $R_3$ can be taken together as $OCH_2O$, $OCH_2CH_2O$ or $CH_2CH_2O$, to form a 5 or 6 membered ring, each of which can be substituted with 1 to 4 halogen atoms or 1 to 2 methyl groups;

$R_5$ is selected from $C(O)OR_{10}$, $C(O)R_{10}$, $C(O)NR_{10}R_{11}$, $C(S)SR_{10}$, $C(S)NR_{10}R_{11}$ and $S(O)_2NR_{10}R_{11}$;

$R_6$ is H or $C_1$ to $C_4$ alkyl;

$R_7$ is H or $CH_3$;

$R_8$ and $R_{10}$ are independently selected from H, $C_1$ to $C_4$ alkyl, $C_3$ to $C_4$ alkenyl, $C_3$ to $C_4$ alkynyl, $C_1$ to $C_4$ haloalkyl, $C_3$ to $C_4$ haloalkenyl, $C_1$ to $C_4$ alkyl substituted with CN, $C(O)OCH_3$, $C(O)OCH_2CH_3$, $OCH_3$, $OCH_2CH_3$, $SCH_3$, $SCH_2CH_3$ and $NO_2$, and phenyl or benzyl, either optionally substituted with W, or $R_8$ and $R_9$ can be taken together as $(CH_2)_4$, $(CH_2)_5$ or $CH_2CH_2OCH_2CH_2$;

$R_9$ and $R_{11}$ are independently selected from H, $C_1$ to $C_4$ alkyl, $C_3$ to $C_4$ alkenyl, $C_3$ to $C_4$ alkynyl, and $C_1$ to $C_4$ haloalkyl, or $R_{10}$ and $R_{11}$ can be taken together as $(CH_2)_4$, $(CH_2)_5$ or $CH_2CH_2OCH_2CH_2$;

m and n are independently 0 to 5;

p is 0 to 4;

W is selected from halogen, CN, $NO_2$, $C_1$ to $C_2$ alkyl, $C_1$ to $C_2$ haloalkyl, $C_1$ to $C_2$ alkoxy, $C_1$-$C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;

X is O or S; and

Y is selected from H, $C_1$ to $C_6$ alkyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, and phenylthio substituted with 1 to 3 substituents independently selected from W.

Preferred compounds A are those of Formula I wherein:

$R_6$ is H;

$R_7$ is H;

n and p are independently 0 to 2; and m is 1 to 2.

Preferred compounds B are preferred compounds A wherein:

$R_1$, $R_2$, $R_3$ are independently $R_8$, halogen, CN, $NO_2$, $OR_8$, $SR_8$, $S(O)R_8$, $S(O)_2R_8$ or $NR_8R_9$, or when m, n or p is 2, $R_1$, $R_2$ or $R_3$ can be taken together as $OCH_2O$, $OCH_2CH_2O$ or $CH_2CH_2O$, each of which can be substituted with 1 to 4 halogen atoms or 1 to 2 methyl groups;

$R_8$ is $C_1$ to $C_2$ alkyl, $C_3$ to $C_4$ alkenyl, $C_1$ to $C_2$ haloalkyl, $C_3$ to $C_4$ haloalkenyl or phenyl optionally substituted with halogen;

$R_9$ is H or $C_1$ to $C_2$ alkyl; and

X is O.

Preferred compounds C are preferred compounds B wherein:

$R_1$ is halogen, CN, $NO_2$, $OCF_2H$, $OCF_3$ $OCF_2CF_2H$, $CF_3$ or when m is 2 then $R_1$ may be taken together as $CH_2C(CH_3)_2O$ or $CF_2CF_2O$ to form a 5 membered ring.

$R_2$ is H, halogen, CN, $NO_2$, $OCH_3$, $OCF_2H$, $OCR_3$, $SCH_3$, $SCF_2H$, $SCR_3$, $CR_3$, $OCF_2CF_2H$ or phenoxy;

$R_3$ is halogen;

$R_5$ is $C(O)OR_{10}$, $C(O)R_{10}$, $C(O)NR_{10}R_{11}$ or $S(O)_2NR_{10}R_{11}$;

$R_{10}$ is H, $C_1$ to $C_4$ alkyl, $C_3$ to $C_4$ alkenyl, $C_3$ to $C_4$ alkynyl, $C_1$ to $C_4$ haloalkyl, $C_3$ to $C_4$ haloalkenyl, $C_1$ to $C_4$ alkyl substituted with CN, $C(O)OCH_3$, $C(O)OCH_2CH_3$, $OCH_3$, $OCH_2CH_3$, $SCH_3$, $SCH_2CH_3$ and $NO_2$;

$R_{11}$ is H or $C_1$ to $C_2$ alkyl; and

Y is H, $C_1$ to $C_6$ alkyl, CHO, $C_2$ to $C_6$ alkylcarbonyl or $C_2$ to $C_6$ alkoxycarbonyl.

Preferred compounds D are preferred compounds C wherein:

$R_5$ is $C(O)OR_{10}$;

$R_{10}$ is $C_1$ to $C_3$ alkyl, $C_2$ to $C_3$ haloalkyl, propargyl or allyl; and one of $R_3$ or $R_5$ is in the para-position and one of $R_1$ is in the para-position; and Y is H, $CH_3$ $C(O)CH_3$, $C(O)OCH_3$ or CHO.

Specifically preferred compounds are E to L:

E. A compound of Preferred D which is methyl 4-[3-(4-chlorophenyl)-4,5-dihydro-1-[[4-(trifluoromethyl)phenylamino]carbonyl]-1H-pyrazol-4-yl]benzoate;

F. A compound of Preferred D which is methyl 4-[3-(4-chlorophenyl)-1-[(4-chlorophenyl) aminocarbonyl]-4,5-dihydro-1H-pyrazol-4-yl]benzoate;

G. A compound of Preferred D which is methyl 4-[3-(4-fluorophenyl)-4,5-dihydro-1-[[4-(trifluoromethyl)-phenylamino]carbonyl]-1H-pyrazol-4-yl]benzoate;

H. A compound of Preferred D which is methyl 4-[1-(4-chlorophenyl)aminocarbonyl]-[3-(4-fluorophenyl)-4,5-dihydro-1H-pyrazol-4-yl]benzoate;

I. A compound of Preferred D which is ethyl 4-[3-(4-chlorophenyl)-4,5-dihydro-1-[[4-(trifluoromethyl)-phenylamino]carbonyl]-1H-pyrazol-4-yl]benzoate;

J. A compound of Preferred D which is ethyl 4-[1-[(4-bromophenyl)aminocarbonyl]-3-(4-chlorophenyl)-4,5-dihydro-1H-pyrazol-4-yl]benzoate;

K. A compound of Preferred D which is methyl, 4-[3-(4-bromophenyl)-4,5-dihydro-1-[[4-(trifluoromethyl)-phenylamino]carbonyl]-1H-pyrazol-4-yl]benzoate; and L. A compound of Preferred D which is methyl 4-[3-(4-cyanophenyl)-4,5-dihydro-1-[[4-(trifluoromethyl)-phenylamino]carbonyl]-1H-pyrazol-4-yl]benzoate.

Hereafter for the sake of brevity, the compounds of this invention are described and claimed as "triphenyl pyrazoline(s)" or "pyrazoline(s)" or "compound(s)", it being understood that such terms include all geometric and stereoisomers and all agriculturally suitable salts of said compounds.

DETAILS OF THE INVENTION

Compounds of Formula I can be prepared from deoxybenzoins of Formula II by a three-step process whereby the Formula II compound is condensed with an aldehyde or ketone, then cyclized with hydrazine and finally reacted with a suitably substituted aryl isocyanate to yield the Formula I compound (Scheme I). Examples of this procedure, where $R_6$ and $R_7$ are equal to hydrogen, can be found in U.S. Pat. No. 4,070,365.

An alternative procedure, where $R_6$ and $R_7$ is other than hydrogen, involves first alkylation of the Formula II compound with an alkyl halide followed by bromination/dehydrobromination to yield the $\alpha,\beta$-unsaturated ketone IIA. Subsequent reactions with hydrazine and an aryl isocyanate yield the compounds of Formula I (Scheme IA). Examples of this procedure are described in European Patent Application 4,733.

Scheme I

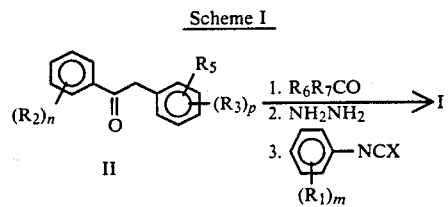

Scheme IA

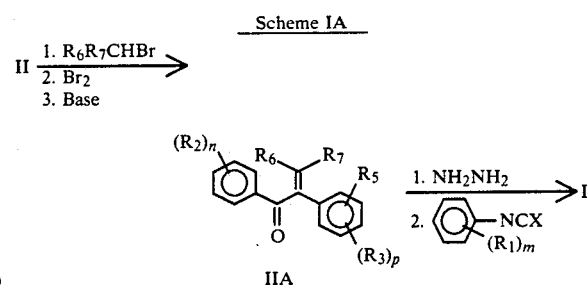

The intermediate deoxybenzoin of Formula II can be prepared by various procedures known in the art. The particular method chosen will depend on the substituents $R_2$, $R_3$, and $R_5$ and their compatibility with the conditions and reagents of that method. For example, compounds of Formula II, where $R_5$ is alkoxycarbonyl or dialkylsulfamoyl, can be prepared by the alkylation of a trimethylsilyl cyanohydrin of Formula III with a benzyl halide of Formula IV followed by conversion of the alkylated trimethylsilyl cyanohydrin to the corresponding carbonyl. The alkylation is typically run in a solvent such as ether or tetrahydrofuran at temperatures in the range of $-78°$ to 25° C. Deprotonation of the Formula III compound is accomplished by treatment with a strong base such as lithium diisopropylamide and the Formula IV compound is subsequently added. Once alkylation is complete, the trimethylsilyl cyanohydrin of Formula V is converted to the deoxybenzoin of Formula II by procedures documented in the art. One method involves treatment of the Formula V compound with fluoride resulting in direct formation of the compounds of Formula II. Alternatively, the Formula II compounds can be prepared from the intermediates of Formula V by acid catalyzed cleavage of the trimethylsilyl group followed by base catalyzed regeneration of the carbonyl. These procedures are depicted in Scheme II.

Scheme II

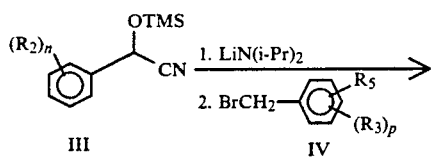

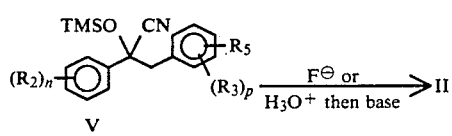

Alternatively, compounds of Formula II are accessible via a Friedel-Crafts acylation as depicted in Scheme III. This procedure is particularly useful for the preparation of a variety of $R_5$ substituents including $C(O)_2R_{10}$, $C(O)NR_{10}R_{11}$ and $SO_2NR_{10}R_{11}$. Generally, best results are achieved when $R_2$ is an ortho-para directing group such as alkyl, halogen, alkoxy and the like.

Scheme III

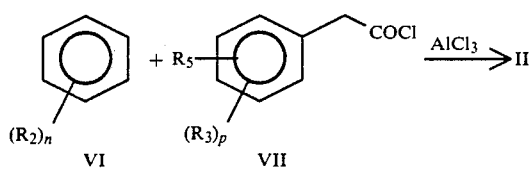

Compounds of Formula II where $R_5$ is $C(O)R_{10}$ can be prepared as outlined in Scheme IV from the corresponding bromo derivative IX by metal-halogen exchange followed by reaction with an electrophilic $C(O)R_{10}$ reagent. Dialkylamides (e.g., dimethylformamide, dimethylacetamide) are particularly suitable reagents for this transformation. Removal of the carbonyl protecting group affords the Formula II compound.

Scheme IV

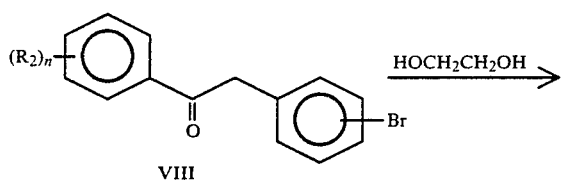

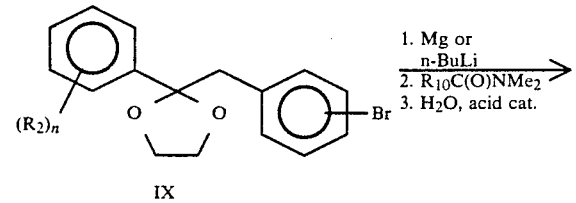

-continued
Scheme IV

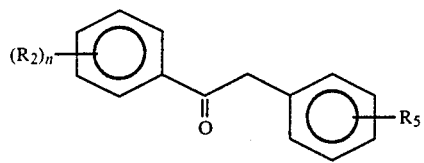

II ($R_5$ is $C(O)R_{10}$)

Trimethylsilyl cyanohydrins of Formula III can be prepared from the corresponding benzaldehyde derivatives by reaction with trimethylsilylnitrile in the presence of a Lewis acid catalyst such as zinc iodide; see Evans et al., *J. Chem. Soc. Chem. Comm.*, 55 (1973).

The following Examples illustrate preparation of the compounds of this invention.

EXAMPLE 1

Step A

4-Chloro-α-(trimethylsilyloxy)benzeneacetonitrile

To a mixture of 32 g of 4-chlorobenzaldehyde and 0.4 g zinc iodide in 40 ml of methylene chloride was added 25 g of trimethylsilylnitrile dropwise under nitrogen. The addition was initiated at room temperature and added at such a rate that gentle reflux of the methylene chloride was maintained. After 24 hours, the reaction was concentrated and the residual oil distilled at 1.0 mm (bath temperature 150° C.) using a Kugelrohr apparatus to afford 50.74 g of the title compound as a yellow oil.

$^1$H NMR (CDCl$_3$) δ 0.24 (s, 9H);
5.50 (s, 1H);
7.41 (s, 4H).

Step B

Methyl 4-(bromomethyl)benzoate

To a solution of 10 g of methyl 4-hydroxymethylbenzoate and 80 g of carbon tetrabromide in 300 ml of diethyl ether was added 63.2 g of triphenylphosphine. The reaction was warmed to room temperature overnight, filtered through Celite ® and concentrated to 87.2 g of a yellow oil. Chromatography on silica gel (95:5, hexane:ethyl acetate) afforded 19.62 g of a white solid, m.p. 52° to 55° C.

$^1$H NMR (CDCl$_3$) δ 3.92 (s, 3H);
4.50 (s, 2H);
7.45 (d, 2H);
8.01 (d, 2H)

Step C

Methyl 4- 2-(4-chlorophenyl)-2-oxoethyl benzoate

To a −70° C. solution of 2.0 ml of diisopropylamine in 20 ml of THF, under nitrogen, was added 5.1 ml of 2.5 M n-butyllithium and the mixture was stirred for 5 min. A solution of 3.0 g of 4-chloro-α-(trimethylsilyloxy)benzeneacetonitrile in 5 to 10 ml of THF was then added dropwise such that the reaction was maintained at less than −60° C. Once added the reaction was stirred for 15 min, and then a solution of methyl 4-(bromomethyl)benzoate in 5 to 10 ml of THF was added dropwise and the reaction was then gradually warmed to room temperature. After 24 hours, 40 ml of 5% aqueous sodium bicarbonate was added and the reaction was concentrated. The residue was dissolved in 50 ml of methanol and 4.0 g of potassium fluoride was added. After stirring for 4 hours, the reaction was concentrated and the residue was partitioned between chloroform and water. The chloroform extracts were dried over magnesium sulfate and concentrated to 3.6 g of an orange solid. Trituration with n-butyl chloride afforded 2.5 g of a white solid, m.p. 165° to 167° C.

$^1$H NMR (CDCl$_3$) δ 3.90 (s, 3H);
4.32 (s, 2H);
7.32 (d, 2H);
7.44 (d, 2H);
7.97 (d, 2H);
8.01 (d, 2H).
IR (Nujol) 1680, 1710 cm$^{-1}$.

Step D

Methyl 4-[3-(4-chlorophenyl)-4,5-dihydro-1H-pyrazol-4-yl]benzoate

A mixture of 2.0 g of the title ester of Step C, 3.0 ml of 37% formaldehyde, 0.2 ml of piperidine and 0.2 ml of glacial acetic acid was heated at reflux, under nitrogen, for 2 hours after which time TLC indicated the reaction was complete. The mixture was cooled to room temperature, partitioned between CHCl$_3$ and 5% aqueous NaHCO$_3$, dried over magnesium sulfate, filtered and concentrated to afford 2.5 g of a yellow oil. The residual oil was taken up in 10 ml of methanol and 0.35 ml of hydrazine hydrate was added. After heating at reflux for 2 hours, a white solid began to precipitate. The reaction was cooled to room temperature, filtered and dried to afford 0.76 g of a pale yellow powder, m.p. 155° to 159° C.

$^1$H NMR (CDCl$_3$) δ 3.58 (dd, 1H);
3.89 (s, 3H);
4.02 (dd, 1H);
4.55 (dd, 1H);
7.1-7.3 (m, 4H);
7.47 (d, 2H);
7.97 (d, 2H).

Step E

Methyl 4-[3-(4-chlorophenyl)-4,5-dihydro-1-[[4-(trifluoromethyl)-phenylamino]carbonyl-1H-pyrazol-4-yl]benzoate A mixture of 0.31 g of the title ester of Step D and 0.19 g of 4-trifluoromethylphenylisocyanate in 8 ml of 1:1 ether-THF was stirred 24 hours at room temperature and then concentrated. Trituration of the residue with ether/hexane afforded 0.28 g of the title compound as a yellow solid, m.p. 168° to 171° C.

$^1$H NMR (CDCl$_3$) δ 3.90 (s, 3H);
4.10 (dd, 1H);
4 45 (t, 1H);
4.82 (dd, 1H);
7.2-8.1 (m, 12H);
8.1 (bs, 1H).

By the general procedures described therein, or obvious modifications thereof, the compounds of Tables 1 to 3 can be prepared.

General Structure for Tables 1 to 3

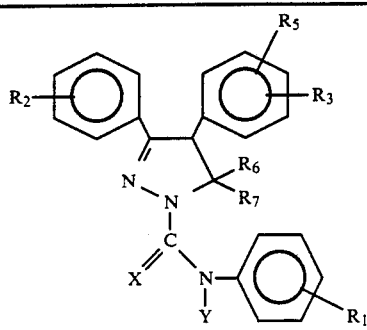

| Table | |
|---|---|
| 1 | X is O, R$_6$ is H, R$_7$ is H |
| 2 | X is S, R$_6$ is H, R$_7$ is H |
| 3 | X is O, Y is H |

The following numbering system describes the compounds of Tables 1 to 3.

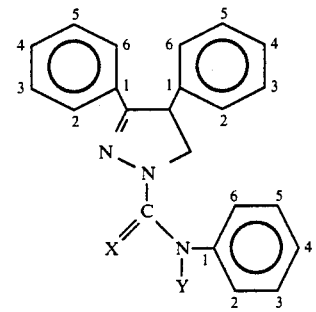

TABLE 1

| R$_1$ | R$_2$ | R$_3$ | R$_5$ | Y | Phys. Prop. |
|---|---|---|---|---|---|
| 4-CF$_3$ | H | H | 4-CO$_2$Me | H | m.p. 149 to 150.5° C. |
| 4-Cl | H | H | 4-CO$_2$Me | H | m.p. 168 to 170° C. |
| 4-Br | H | H | 4-CO$_2$Me | H | m.p. 172 to 174° C. |
| 4-OCF$_2$H | H | H | 4-CO$_2$Me | H | |
| 4-F | H | H | 4-CO$_2$Me | H | |
| 4-OCF$_3$ | H | H | 4-CO$_2$Me | H | |
| 4-CF$_3$-3-Cl | H | H | 4-CO$_2$Me | H | |
| 4-SCF$_2$H | H | H | 4-CO$_2$Me | H | |
| 4-NO$_2$ | H | H | 4-CO$_2$Me | H | |
| 4-CO$_2$Me | H | H | 4-CO$_2$Me | H | |
| 4-OMe | H | H | 4-CO$_2$Me | H | |
| 3,4-OCF$_2$CF$_2$ | H | H | 4-CO$_2$Me | H | |
| 3,4-di-Cl | H | H | 4-CO$_2$Me | H | |
| 4-Cl | 4-Cl | H | 4-CO$_2$Me | H | m.p. 132 to 133° C. |
| 4-Br | 4-Cl | H | 4-CO$_2$Me | H | m.p. 140 to 145° C. |
| 4-OCF$_2$H | 4-Cl | H | 4-CO$_2$Me | H | |
| 4-F | 4-Cl | H | 4-CO$_2$Me | H | |
| 4-OCF$_3$ | 4-Cl | H | 4-CO$_2$Me | H | |
| 4-SCF$_2$H | 4-Cl | H | 4-CO$_2$Me | H | |
| 4-CO$_2$-i-C$_3$H$_7$ | 4-Cl | H | 4-CO$_2$Me | H | |

TABLE 1-continued

| R₁ | R₂ | R₃ | R₅ | Y | Phys. Prop. |
|---|---|---|---|---|---|
| 3,4-OCF₂CF₂¹ | 4-Cl | H | 4-CO₂Me | H | |
| 4-Cl | 4-F | H | 4-CO₂Me | H | m.p. 145 to 147° C. |
| 4-CF₂H | 4-F | H | 4-CO₂Me | H | |
| 4-OCF₂H | 4-F | H | 4-CO₂Me | H | |
| 4-SCF₂H | 4-F | H | 4-CO₂Me | H | |
| 4-Br | 4-F | H | 4-CO₂Me | H | |
| 4-F | 4-F | H | 4-CO₂Me | H | |
| 3-CF₃-4-Cl | 4-F | H | 4-CO₂Me | H | |
| 4-CF₃ | 4-F | H | 4-CO₂Me | H | m.p. 148 to 150° C. |
| 4-OCF₃ | 4-F | H | 4-CO₂Me | H | |
| 4-CF₃ | 4-Cl | H | 4-CO₂Et | H | m.p. 167 to 168° C. |
| 4-Cl | 4-Cl | H | 4-CO₂Et | H | m.p. 144 to 147° C. |
| 4-Br | 4-Cl | H | 4-CO₂Et | H | m.p. 158 to 160° C. |
| 4-SMe | 4-Cl | H | 4-CO₂Et | H | m.p. 145 to 155° C. |
| 4-OCF₃ | 4-Cl | H | 4-CO₂Et | H | |
| 4-OCF₂H | 4-Cl | H | 4-CO₂Et | H | |
| 4-CF₃ | 4-Cl | H | 4-CO₂H | H | |
| 4-Cl | 4-Cl | H | 4-CO₂H | H | |
| 4-Br | 4-Cl | H | 4-CO₂H | H | |
| 4-F | 4-Cl | H | 4-CO₂H | H | |
| 4-OCF₃ | 4-Cl | H | 4-CO₂H | H | |
| 4-OCF₂H | 4-Cl | H | 4-CO₂H | H | |
| 4-CF₃ | 4-Cl | H | 4-CO₂-i-Pr | H | m.p. 191 to 193° C. |
| 4-Cl | 4-Cl | H | 4-CO₂-i-Pr | H | m.p. 191 to 193° C. |
| 4-Br | 4-Cl | H | 4-CO₂-i-Pr | H | m.p. 204 to 206° C. |
| 4-SMe | 4-Cl | H | 4-CO₂-i-Pr | H | m.p. 171 to 174° C. |
| 4-CF₃ | 4-Cl | H | 4-CO₂CH₂CF₃ | H | m.p. 152 to 153.5° C. |
| 4-Cl | 4-Cl | H | 4-CO₂CH₂CF₃ | H | m.p. 124 to 126° C. |
| 4-Br | 4-Cl | H | 4-CO₂CH₂CF₃ | H | m.p. 133 to 134° C. |
| 4-SMe | 4-Cl | H | 4-CO₂CH₂CF₃ | H | |
| 4-CF₃ | 3-Cl | H | 4-CO₂Me | H | m.p. 136 to 139° C. |
| 4-Cl | 3-Cl | H | 4-CO₂Me | H | m.p. 188 to 189° C. |
| 4-Br | 3-Cl | H | 4-CO₂Me | H | |
| 4-OCF₂H | 3-Cl | H | 4-CO₂Me | H | |
| 4-OCF₃ | 3-Cl | H | 4-CO₂Me | H | |
| 3,4-di-Cl | 3-Cl | H | 4-CO₂Me | H | m.p. 100 to 104° C. |
| 4-CF₃ | 3-Cl | H | 4-CO₂Et | H | |
| 4-Cl | 3-Cl | H | 4-CO₂Et | H | |
| 4-Br | 3-Cl | H | 4-CO₂Et | H | |
| 4-OCF₂H | 3-Cl | H | 4-CO₂Et | H | |
| 4-CF₃ | 4-CO₂Me | H | 4-CO₂Me | H | m.p. 190 to 200° C. |
| 4-Cl | 4-CO₂Me | H | 4-CO₂Me | H | m.p. 180 to 190° C. (d) |
| 4-CO₂Et | 4-CO₂Me | H | 4-CO₂Me | H | m.p. 168 to 170° C. |
| 3-CF₃ | 4-CO₂Me | H | 4-CO₂Me | H | m.p. 178 to 181° C. |
| 4-OCH₃ | 4-CO₂Me | H | 4-CO₂Me | H | m.p. 151 to 153° C. |
| 4-CF₃ | 4-OPh | H | 4-CO₂Me | H | m.p. 156 to 158° C. |
| 4-Cl | 4-OPh | H | 4-CO₂Me | H | m.p. 175 to 177° C. |
| 4-Br | 4-OPh | H | 4-CO₂Me | H | m.p. 172 to 176° C. |
| 4-CF₃ | 3,4-di-Cl | H | 4-CO₂Me | H | m.p. 202 to 204° C. |
| 4-Cl | 3,4-di-Cl | H | 4-CO₂Me | H | m.p. 187 to 189° C. |
| 4-Br | 3,4-di-Cl | H | 4-CO₂Me | H | m.p. 191 to 192° C. |
| 3,4-di-Cl | 3,4-di-Cl | H | 4-CO₂Me | H | m.p. 174.5 to 176° C. |
| 4-CF₃ | 4-Cl | H | 4-CO₂CH₂C≡CH | H | m.p. 108 to 112° C. |
| 4-Cl | 4-Cl | H | 4-CO₂CH₂C≡CH | H | m.p. 139 to 141° C. |
| 4-Br | 4-Cl | H | 4-CO₂CH₂C≡CH | H | m.p. 144 to 147° C. |
| 4-OCF₃ | 4-Cl | H | 4-CO₂CH₂C≡CH | H | |
| 4-OCF₂H | 4-Cl | H | 4-CO₂CH₂C≡CH | H | |
| 4-F | 4-Cl | H | 4-CO₂CH₂C≡CH | H | |
| 4-CF₃ | 4-F | H | 4-CO₂CH₂C≡CH | H | |
| 4-Cl | 4-F | H | 4-CO₂CH₂C≡CH | H | |
| 4-Br | 4-F | H | 4-CO₂CH₂C≡CH | H | |
| 4-CF₃ | 4-Br | H | 4-CO₂CH₂C≡CH | H | |
| 4-Cl | 4-Br | H | 4-CO₂CH₂C≡CH | H | |
| 4-CF₃ | 4-CF₃ | H | 4-CO₂Me | H | m.p. 179 to 179.5° C. |
| 4-Cl | 4-CF₃ | H | 4-CO₂Me | H | m.p. 155 to 158° C. |
| 4-Br | 4-CF₃ | H | 4-CO₂Me | H | |
| 4-OCF₂H | 4-CF₃ | H | 4-CO₂Me | H | |
| 4-OCF₃ | 4-CF₃ | H | 4-CO₂Me | H | |
| 4-CF₃ | 4-OCF₂H | H | 4-CO₂Me | H | oil |
| 4-Cl | 4-OCF₂H | H | 4-CO₂Me | H | |
| 4-Br | 4-OCF₂H | H | 4-CO₂Me | H | |
| 4-OCF₂H | 4-OCF₂H | H | 4-CO₂Me | H | |
| 4-OCF₃ | 4-OCF₂H | H | 4-CO₂Me | H | |
| 4-CF₃ | 4-OCF₃ | H | 4-CO₂Me | H | m.p. 137 to 138.5° C. |
| 4-Cl | 4-OCF₃ | H | 4-CO₂Me | H | m.p. 105 to 107° C. |
| 4-Br | 4-OCF₃ | H | 4-CO₂Me | H | m.p. 106 to 108° C. |
| 4-OCF₂H | 4-OCF₂H | H | 4-CO₂Me | H | |
| 4-OCF₃ | 4-OCF₂H | H | 4-CO₂Me | H | |
| 4-CF₃ | 4-SMe | H | 4-CO₂Me | H | m.p. 207.5 to 208.5° C. |
| 4-Cl | 4-SMe | H | 4-CO₂Me | H | m.p. 131 to 133° C. |
| 4-Br | 4-SMe | H | 4-CO₂Me | H | m.p. 160 to 163° C. |

TABLE 1-continued

| R₁ | R₂ | R₃ | R₅ | Y | Phys. Prop. |
|---|---|---|---|---|---|
| 4-SMe | 4-SMe | H | 4-CO₂Me | H | m.p. 177 to 179° C. |
| 3-Cl-4-F | 4-SMe | H | 4-CO₂Me | H | m.p. 175 to 178° C. |
| 4-Cl | 4-SO₂Me | H | 4-CO₂Me | H | m.p. 138 to 142° C. |
| 4-Br | 4-SO₂Me | H | 4-CO₂Me | H | m.p. 135 to 143° C. |
| 4-CF₃ | 4-SO₂Me | H | 4-CO₂Me | H | m.p. 127 to 133° C. |
| 4-Cl | 4-NMe₂ | H | 4-CO₂Me | H | m.p. 136 to 150° C. |
| 4-Br | 4-NMe₂ | H | 4-CO₂Me | H | m.p. 152 to 160° C. |
| 3-Cl-4-F | 4-NMe₂ | H | 4-CO₂Me | H | m.p. 195 to 204° C. |
| 4-CF₃ | 4-NMe₂ | H | 4-CO₂Me | H | m.p. 190 to 200° C. |
| 4-CF₃ | 3,4-di-F | H | 4-CO₂Me | H | m.p. 189 to 190.5° C. |
| 4-Cl | 3,4-di-F | H | 4-CO₂Me | H | m.p. 170 to 171° C. |
| 4-Br | 3,4-di-F | H | 4-CO₂Me | H | m.p. 176.5 to 178° C. |
| 4-CO₂Et | 3,4-di-F | H | 4-CO₂Me | H | m.p. 160 to 162° C. |
| 4-Cl-3-CF₃ | 3,4-di-F | H | 4-CO₂Me | H | m.p. 106 to 108° C. (d) |
| 4-CF₃ | 4-Br | H | 4-CO₂Me | H | m.p. 188 to 189.5° C. |
| 4-Cl | 4-Br | H | 4-CO₂Me | H | m.p. 152 to 154° C. |
| 4-Br | 4-Br | H | 4-CO₂Me | H | m.p. 154 to 155° C. |
| 4-OCF₂H | 4-Br | H | 4-CO₂Me | H | |
| 4-OCF₃ | 4-Br | H | 4-CO₂Me | H | |
| 4-OCH₃ | 4-Br | H | 4-CO₂Me | H | m.p. 178 to 180° C. |
| 4-CF₃ | 4-Cl | H | 4-CONHMe | H | m.p. 222 to 224° C. |
| 4-Cl | 4-Cl | H | 4-CONHMe | H | m.p. 189 to 191° C. |
| 4-Br | 4-Cl | H | 4-CONHMe | H | |
| 4-F | 4-Cl | H | 4-CONHMe | H | m.p. 187 to 189° C. |
| 3,4-di-Cl | 4-Cl | H | 4-CONHMe | H | m.p. 175 to 177° C. |
| 4-OCF₂H | 4-Cl | H | 4-CONHMe | H | |
| 4-OCF₃ | 4-Cl | H | 4-CONHMe | H | |
| 4-CF₃ | 4-Cl | H | 4-CONMe₂ | H | m.p. 124 to 125° C. |
| 4-Cl | 4-Cl | H | 4-CONMe₂ | H | m.p. 175 to 177° C. |
| 4-Br | 4-Cl | H | 4-CONMe₂ | H | m.p. 198 to 199.5° C. |
| 4-OCF₂H | 4-Cl | H | 4-CONMe₂ | H | |
| 4-OCF₃ | 4-Cl | H | 4-CONMe₂ | H | |
| 4-CF₃ | 4-Cl | H | 4-CONEt₂ | H | |
| 4-Cl | 4-Cl | H | 4-CONEt₂ | H | |
| 4-Br | 4-Cl | H | 4-CONEt₂ | H | |
| 4-OCF₂H | 4-Cl | H | 4-CONEt₂ | H | |
| 4-OCF₃ | 4-Cl | H | 4-CONEt₂ | H | |
| 4-CF₃ | 4-Cl | H | 4-CONH-n-Bu | H | |
| 4-Cl | 4-Cl | H | 4-CONH₂ | H | |
| 4-Br | 4-Cl | H | 4-CONHEt | H | |
| 4-OCF₂H | 4-Cl | H | 4-CONH-i-C₃H₇ | H | |
| 4-OCF₃ | 4-Cl | H | 4-CONH₂ | H | |
| 4-CF₃ | 4-Cl | H | 4-C(O)Me | H | m.p. 255 to 258° C. |
| 4-Cl | 4-Cl | H | 4-C(O)Me | H | m.p. 264 to 266° C. |
| 4-Br | 4-Cl | H | 4-C(O)Me | H | |
| 4-OCF₂H | 4-Cl | H | 4-C(O)Me | H | |
| 4-OCF₃ | 4-Cl | H | 4-C(O)Me | H | |
| 4-CF₃ | 4-Cl | H | 4-C(O)Et | H | |
| 4-Cl | 4-Cl | H | 4-C(O)Et | H | |
| 4-Br | 4-Cl | H | 4-C(O)Et | H | |
| 4-OCF₂H | 4-Cl | H | 4-C(O)Et | H | |
| 4-OCF₃ | 4-Cl | H | 4-C(O)Et | H | |
| 4-CF₃ | 4-Cl | H | 4-CHO | H | |
| 4-Cl | 4-Cl | H | 4-CHO | H | |
| 4-Br | 4-Cl | H | 4-CHO | H | |
| 4-OCF₂H | 4-Cl | H | 4-CHO | H | |
| 4-OCF₃ | 4-Cl | H | 4-CHO | H | |
| 4-CF₃ | 4-Cl | H | 4-C(O)CF₃ | H | |
| 4-Cl | 4-Cl | H | 4-C(O)-n-Bu | H | |
| 4-Br | 4-Cl | H | 4-C(O)(CH₂)₃Cl | H | |
| 4-OCF₂H | 4-Cl | H | 4-C(O)CH₂Br | H | |
| 4-OCF₃ | 4-Cl | H | 4-C(O)-i-C₃H₇ | H | |
| 4-CF₃ | 4-F | H | 4-C(O)Me | H | |
| 4-Cl | 4-F | H | 4-C(O)Me | H | |
| 4-Br | 4-F | H | 4-C(O)Me | H | |
| 4-OCF₂H | 4-F | H | 4-C(O)Me | H | |
| 3,4-OCF₂CF₂¹ | 4-F | H | 4-C(O)Me | H | |
| 4-OCF₃ | 4-OCF₂H | H | 4-C(O)Me | H | |
| 4-CF₃ | 4-OCF₂H | H | 4-C(O)Me | H | |
| 4-Cl | 4-OCF₂H | H | 4-C(O)Me | H | |
| 4-Br | 4-OCF₂H | H | 4-C(O)Me | H | |
| 4-OCF₂H | 4-OCF₂H | H | 4-C(O)Me | H | |
| 3,4-OCF₂CF₂ | 4-OCF₂H | H | 4-C(O)Me | H | |
| 4-OCF₃ | 4-OCF₂H | H | 4-C(O)Me | H | |
| 4-CF₃ | 4-CF₃ | H | 4-C(O)Me | H | |
| 4-Cl | 4-CF₃ | H | 4-C(O)Me | H | |
| 4-Br | 4-CF₃ | H | 4-C(O)Me | H | |
| 4-OCF₂H | 4-CF₃ | H | 4-C(O)Me | H | |
| 3,4-OCF₂CF₂¹ | 4-CF₃ | H | 4-C(O)Me | H | |
| 4-OCF₃ | 4-CF₃ | H | 4-C(O)Me | H | |
| 4-CF₃ | 4-F | H | 4-CHO | H | |

TABLE 1-continued

| R$_1$ | R$_2$ | R$_3$ | R$_5$ | Y | Phys. Prop. |
|---|---|---|---|---|---|
| 4-Cl | 4-F | H | 4-CHO | H | |
| 4-Br | 4-F | H | 4-CHO | H | |
| 4-OCF$_2$H | 4-F | H | 4-CHO | H | |
| 4-CF$_3$ | 4-Cl | H | 4-SO$_2$NMe$_2$ | H | m.p. 199 to 202° C. |
| 4-Cl | 4-Cl | H | 4-SO$_2$NMe$_2$ | H | m.p. 199 to 203° C. |
| 4-Br | 4-Cl | H | 4-SO$_2$NMe$_2$ | H | |
| 4-OCF$_2$H | 4-Cl | H | 4-SO$_2$NMe$_2$ | H | |
| 4-OCF$_3$ | 4-Cl | H | 4-SO$_2$NMe$_2$ | H | |
| 4-CF$_3$ | 4-Cl | H | 4-SO$_2$NHMe | H | m.p. 209 to 212° C. |
| 4-Cl | 4-Cl | H | 4-SO$_2$NHMe | H | m.p. 231 to 234° C. |
| 4-Br | 4-Cl | H | 4-SO$_2$NHEt | H | |
| 4-OCF$_2$H | 4-Cl | H | 4-SO$_2$NH$_2$ | H | |
| 4-OCF$_3$ | 4-Cl | H | 4-SO$_2$NEt$_2$ | H | |
| 4-CF$_3$ | 4-F | H | 4-SO$_2$NMe$_2$ | H | |
| 4-Cl | 4-F | H | 4-SO$_2$NMe$_2$ | H | |
| 4-Br | 4-F | H | 4-SO$_2$NMe$_2$ | H | |
| 4-OCF$_2$H | 4-F | H | 4-SO$_2$NMe$_2$ | H | |
| 4-OCF$_3$ | 4-F | H | 4-SO$_2$NMe$_2$ | H | |
| 4-CF$_3$ | 4-F | H | 4-SO$_2$NH$_2$ | H | |
| 4-Cl | 4-F | H | 4-SO$_2$NHMe | H | |
| 4-Br | 4-F | H | 4-SO$_2$NHEt | H | |
| 4-OCF$_2$H | 4-F | H | 4-SO$_2$NEt$_2$ | H | |
| 4-OCF$_3$ | 4-F | H | 4-SO$_2$NHMe | H | |
| 4-CF$_3$ | 4-F | H | 4-CONHMe | H | |
| 4-Cl | 4-F | H | 4-CONHMe | H | |
| 4-CF$_3$ | 4-F | H | 4-CONMe$_2$ | H | |
| 4-Cl | 4-F | H | 4-CONMe$_2$ | H | |
| 4-CF$_3$ | 4-OCF$_2$H | H | 4-CONHMe | H | |
| 4-Cl | 4-OCF$_2$H | H | 4-CONHMe | H | |
| 4-CF$_3$ | 4-OCF$_2$H | H | 4-CONMe$_2$ | H | |
| 4-Cl | 4-OCF$_2$H | H | 4-CONMe$_2$ | H | |
| 4-CF$_3$ | 4-OCF$_2$H | H | 4-CONH$_2$ | H | |
| 4-Cl | 4-OCF$_2$H | H | 4-CONH$_2$ | H | |
| 4-CF$_3$ | 4-F | H | 4-SO$_2$NMe$_2$ | H | |
| 4-Cl | 4-F | H | 4-SO$_2$NMe$_2$ | H | |
| 4-CF$_3$ | 4-F | H | 4-SO$_2$NHMe | H | |
| 4-Cl | 4-F | H | 4-SO$_2$NHMe | H | |
| 4-CF$_3$ | 4-CF$_3$ | H | 4-SO$_2$NMe$_2$ | H | m.p. 81 to 85° C. |
| 4-Cl | 4-CF$_3$ | H | 4-SO$_2$NMe$_2$ | H | m.p. 85 to 88° C. |
| 4-SMe | 4-CF$_3$ | H | 4-SO$_2$NMe$_2$ | H | m.p. 110 to 114° C. |
| 4-CF$_3$ | 4-CF$_3$ | H | 4-SO$_2$NHMe | H | |
| 4-Cl | 4-CF$_3$ | H | 4-SO$_2$NHMe | H | |
| 4-CF$_3$ | 4-Cl | H | 4-CS$_2$Me | H | |
| 4-Cl | 4-F | H | 4-CS$_2$Me | H | |
| 4-Br | 4-CF$_3$ | H | 4-CS$_2$Et | H | |
| 4-OCF$_2$H | 4-OCF$_2$H | H | 4-CS$_2$Et | H | |
| 4-OCF$_3$ | 4-Cl | H | 4-CSNMe$_2$ | H | |
| 4-CF$_3$ | 4-F | H | 4-CSNMe$_2$ | H | |
| 4-Cl | 4-CF$_3$ | H | 4-CSNHMe | H | |
| 4-Br | 4-OCF$_2$H | H | 4-CSNHMe | H | |
| 4-OCF$_2$H | 4-Cl | H | 4-CSNH$_2$ | H | |
| 4-CF$_3$ | 4-F | H | 4-CSNH$_2$ | H | |
| 4-Cl | 4-CF$_3$ | H | 4-CO$_2$-allyl | H | |
| 4-Br | 4-OCF$_2$H | H | 4-CO$_2$-allyl | H | |
| 4-OCF$_2$H | 4-Cl | H | 4-CO$_2$-allyl | H | |
| 4-OCF$_3$ | 4-F | H | 4-CO$_2$CH$_2$Ph | H | |
| 4-CF$_3$ | 4-CF$_3$ | H | 4-CO$_2$CH$_2$Ph | H | |
| 4-Cl | 4-OCF$_2$H | H | 4-CO$_2$CH$_2$OMe | H | |
| 4-Br | 4-Cl | H | 4-CO$_2$CH$_2$CN | H | |
| 4-OCF$_2$H | 4-F | H | 4-CO$_2$CH2CH$_2$CN | H | |
| 4-Cl | 4-Cl | H | 4-CO$_2$CH$_2$SM3 | H | |
| 4-CF$_3$ | 4-F | H | 4-CO$_2$CH$_2$CH$_2$NO$_2$ | H | |
| 4-CF$_3$ | 4-Cl | 4-Cl | 3-CO$_2$Me | H | m.p. 173 to 175° C. |
| 4-CF$_3$ | 4-Cl | 4-F | 3-CO$_2$Me | H | |
| 4-CF$_3$ | 4-Cl | 4-OCF$_2$H | 3-CO$_2$Me | H | |
| 4-CF$_3$ | 4-Cl | H | 3-CO$_2$Me | H | m.p. 168 to 168.5° C. |
| 4-Cl | 4-Cl | H | 3-CO$_2$Me | H | m.p. 164 to 168° C. |
| 4-Br | 4-Cl | H | 3-CO$_2$Me | H | m.p. 160.5 to 163° C. |
| 4-CO$_2$Et | 4-Cl | H | 3-CO$_2$Me | H | m.p. 186 to 187° C. |
| 4-CF$_3$ | 4-Cl | 4-Cl | 2-CO$_2$Me | H | |
| 4-CF$_3$ | 4-Cl | 4-F | 2-CO$_2$Me | H | |
| 4-CF$_3$ | 4-Cl | 4-OCF$_2$H | 2-CO$_2$Me | H | |
| 4-CF$_3$ | 4-Cl | 4-Cl | 3-C(O)Me | H | |
| 4-CF$_3$ | 4-Cl | 4-F | 3-C(O)Me | H | |
| 4-CF$_3$ | 4-Cl | 4-OCF$_2$H | 3-C(O)Me | H | |
| 4-CF$_3$ | 4-Cl | 4-Cl | 3-CONME$_2$ | H | |
| 4-CF$_3$ | 4-Cl | 4-F | 3-CONME$_2$ | H | |
| 4-CF$_3$ | 4-Cl | 4-OCF$_2$H | 3-CONME$_2$ | H | |
| 4-CF$_3$ | 4-F | 4-Cl | 3-CO$_2$Me | H | |
| 4-CF$_3$ | 4-F | 4-F | 3-CO$_2$Me | H | |
| 4-CF$_3$ | 4-F | 4-OCF$_2$H | 3-CO$_2$Me | H | |

TABLE 1-continued

| R₁ | R₂ | R₃ | R₅ | Y | Phys. Prop. |
|---|---|---|---|---|---|
| 4-CF₃ | 4-OCF₂H | 4-Cl | 3-CO₂Me | H | |
| 4-CF₃ | 4-OCF₂H | 4-F | 3-CO₂Me | H | |
| 4-CF₃ | 4-OCF₂H | 4-OCF₂H | 3-CO₂Me | H | |
| 4-Cl | 4-Cl | 4-Cl | 3-CO₂Me | H | m.p. 187 to 188° C. |
| 4-Br | 4-Cl | 4-Cl | 3-CO₂Me | H | |
| 4-Cl | 4-Cl | 4-Cl | 3-CO₂Me | H | |
| 4-Cl-3-NO₂ | 4-Cl | 4-Cl | 3-CO₂Me | H | |
| 4-CF₃ | 4-Cl | 3-Cl | 4-CO₂Me | H | |
| 4-CF₃ | 4-Cl | 3-F | 4-CO₂Me | H | |
| 4-CF₃ | 3,4-di-Cl | H | 4-CHO | H | |
| 4-CF₃ | 3,4-di-Cl | H | 4-CONMe₂ | H | |
| 4-CF₃ | 3,4-di-Cl | H | 4-SO₂NMe₂ | H | |
| 4-CF₃ | 3,4-di-Cl | H | 4-C(O)Me | H | |
| 4-CF₃ | 3-Cl-4-OCF₂H | H | 4-CO₂Me | H | |
| 4-CF₃ | 3-Cl-4-OCF₂H | H | 4-CHO | H | |
| 4-CF₃ | 3-Cl-4-OCF₂H | H | 4-CONMe₂ | H | |
| 4-CF₃ | 3-Cl-4-OCF₂H | H | 4-SO₂NMe₂ | H | |
| 4-CF₃ | 3-Cl-4-OCF₂H | H | 4-C(O)Me | H | |
| 4-CF₃ | 3-Cl-4-OCF₃ | H | 4-CO₂Me | H | |
| 4-CF₃ | 3-Cl-4-OCF₃ | H | 4-CHO | H | |
| 4-CF₃ | 3-Cl-4-OCF₃ | H | 4-CONMe₂ | H | |
| 4-CF₃ | 3-Cl-4-OCF₃ | H | 3-SO₂NMe₂ | H | |
| 4-CF₃ | 3-Cl-4-OCF₃ | H | 4-C(O)Me | H | |
| 4-CF₃ | 3,4-di-F | H | 4-CONMe₂ | H | |
| 4-CF₃ | 3,4-di-F | H | 4-CHO | H | |
| 4-CF₃ | 3,4-di-F | H | 4-SO₂NMe₂ | H | |
| 4-CF₃ | 3,4-di-F | H | 4-C(O)Me | H | |
| 4-CF₃ | 4-CN | H | 4-CO₂Me | H | m.p. 169 to 170.5° C. |
| 4-Cl | 4-CN | H | 4-CO₂Me | H | m.p. 112 to 116° C. |
| 4-Br | 4-CN | H | 4-CO₂Me | H | |
| 4-OCF₂H | 4-CN | H | 4-CO₂Me | H | |
| 4-OCF₃ | 4-CN | H | 4-CO₂Me | H | |
| 3,4-di-Cl | 4-CN | H | 4-CO₂Me | H | m.p. 134 to 137° C. |
| 4-CF₃ | 4-SCN | H | 4-CO₂Me | H | |
| 4-CF₃ | 4-NO₂ | H | 4-CO₂Me | H | |
| 4-CF₃ | 4-OEt | H | 4-CO₂Me | H | |
| 4-CF₃ | 4-O-allyl | H | 4-CO₂Me | H | m.p. 168 to 169° C. |
| 4-CF₃ | 4-OCH₂C(Cl)=CH₂ | H | 4-CO₂Me | H | |
| 4-CF₃ | 4-SCF₂CF₂H | H | 4-CO₂Me | H | |
| 4-CF₃ | 4-S(O)Me | H | 4-CO₂Me | H | |
| 4-CF₃ | 4-SO₂NMe₂ | H | 4-CO₂Me | H | |
| 4-CF₃ | 4-NMe₂ | H | 4-CO₂Me | H | |
| 4-CF₃ | 4-NEt₂ | H | 4-CO₂Me | H | |
| 4-Cl | 4-NHCHO | H | 4-CO₂Me | H | |
| 4-Cl | 4-OC(O)NHMe | H | 4-CO₂Me | H | |
| 4-Cl | 4-NHSO₂Me | H | 4-CO₂Me | H | |
| 4-Cl | 3,4-OCH₂O | H | 4-CO₂Me | H | |
| 4-Cl | 3,4-OCF₂CF₂¹ | H | 4-CO₂Me | H | |
| 4-Cl | 3,4-OCF₂CF₂O¹ | H | 4-CO₂Me | H | |
| 4-Cl | 4-OC(O)Me | H | 4-CO₂Me | H | |
| 4-Cl | 4-OSO₂Ph | H | 4-CO₂Me | H | |
| 4-Cl | 4-Ph | H | 4-CO₂Me | H | |
| 4-Cl | 4-OPh | H | 4-CO₂Me | H | |
| 4-Cl | 4-allyl | H | 4-CO₂Me | H | |
| 4-Cl | 4-CH₂CN | H | 4-CO₂Me | H | |
| 4-OCF₂CF₂H | 4-Cl | H | 4-CO₂Me | H | |
| 4-SCF₂CF₂H | 4-Cl | H | 4-CO₂Me | H | |
| 4-CN | 4-Cl | H | 4-CO₂Me | H | |
| 3,4-di-Cl | 4-Cl | H | 4-CO₂Me | H | |
| 4-CO₂Me | 4-Cl | H | 4-CO₂Me | H | |
| 4-CF₂Cl | 4-Cl | H | 4-CO₂Me | H | |
| 4-CO₂Et | 4-Cl | H | 4-CO₂Me | H | m.p. 186 to 188° C. |
| 4-NMe₂ | 4-Cl | H | 4-CO₂Me | H | |
| 4-SO₂Me | 4-Cl | H | 4-CO₂Me | H | |
| 4-SMe | 4-Cl | H | 4-CO₂Me | H | m.p. 191.5 to 193° C. |
| 4-S(O)Me | 4-Cl | H | 4-CO₂Me | H | |
| 4-SO₂NMe₂ | 4-Cl | H | 4-CO₂Me | H | |
| 3,4-CH₂CMe₂O¹ | 4-Cl | H | 4-CO₂Me | H | |
| 3,4-OCMe₂CH₂¹ | 4-Cl | H | 4-CO₂Me | H | |
| 4-SCN | 4-Cl | H | 4-CO₂Me | H | |
| 4-CF₃-3-Cl | 4-Cl | H | 4-CO₂Me | H | |
| 4-Ph | 4-Cl | H | 4-CO₂Me | H | |
| 4-(4-Cl-Ph) | 4-Cl | H | 4-CO₂Me | H | |
| 4-OPh | 4-Cl | H | 4-CO₂Me | H | |
| 4-CH₂Ph | 4-Cl | H | 4-CO₂Me | H | |
| 3-NO₂-4-Cl | 4-Cl | H | 4-CO₂Me | H | m.p. 142 to 151° C. (d) |
| 2-OMe-4-Cl | 4-Cl | H | 4-CO₂Me | H | m.p. 180 to 185° C. |
| 3-Cl-4-F | 4-Cl | H | 4-CO₂Me | H | m.p. 165 to 168° C. |
| 3-CF₃-4-Cl | 4-Cl | H | 4-CO₂Me | H | m.p. 120 to 129° C. |
| 3,4-di-Cl | 4-Cl | H | 4-CO₂Me | H | m.p. 235 to 243° C. |
| 4-CF₃ | 4-Cl | H | 4-CO₂Me | Me | m.p. 92 to 98° C. |

TABLE 1-continued

| R₁ | R₂ | R₃ | R₅ | Y | Phys. Prop. |
|---|---|---|---|---|---|
| 4-Cl | 4-Cl | H | 4-CO₂Me | Me | m.p. 90 to 95° C. |
| 4-Br | 4-Cl | H | 4-CO₂Me | Me | m. p. 82 to 86° C. |
| 4-OCF₂H | 4-Cl | H | 4-CO₂Me | Me | |
| 4-OCF₃ | 4-Cl | H | 4-CO₂Me | Me | |
| 4-CF₃ | 4-F | H | 4-CO₂Me | Me | |
| 4-Cl | 4-F | H | 4-CO₂Me | Me | |
| 4-OCF₂H | 4-F | H | 4-CO₂Me | Me | |
| 4-OCF₃ | 4-F | H | 4-CO₂Me | | |
| 4-OCF₂H | 4-F | H | 4-CO₂Me | Me | |
| 4-OCF₃ | 4-F | H | 4-CO₂Me | Me | |
| 4-CF₃ | 4-Cl | H | 4-CO₂Me | C(O)Me | |
| 4-Cl | 4-Cl | H | 4-CO₂Me | C(O)Me | |
| 4-OCF₂H | 4-Cl | H | 4-CO₂Me | C(O)Me | |
| 4-OCF₃ | 4-Cl | H | 4-CO₂Me | C(O)Me | |
| 4-CF₃ | 4-F | H | 4-CO₂Me | C(O)Me | |
| 4-Cl | 4-F | H | 4-CO₂Me | C(O)Me | |
| 4-OCF₂H | 4-F | H | 4-CO₂Me | C(O)Me | |
| 4-OCF₃ | 4-F | H | 4-CO₂Me | C(O)Me | |
| 4-CF₃ | 4-Cl | H | 4-CO₂Me | CO₂Me | |
| 4-Cl | 4-Cl | H | 4-CO₂Me | CO₂Me | |
| 4-OCF₂H | 4-Cl | H | 4-CO₂Me | CO₂Me | |
| 4-OCF₃ | 4-Cl | H | 4-CO₂Me | CO₂Me | |
| 4-CF₃ | 4-F | H | 4-CO₂Me | CO₂Me | |
| 4-Cl | 4-F | H | 4-CO₂Me | CO₂Me | |
| 4-OCF₂H | 4-F | H | 4-CO₂Me | CO₂Me | |
| 4-CF₃ | 4-Cl | H | 4-CO₂Me | CHO | |
| 4-Cl | 4-Cl | H | 4-CO₂Me | CHO | |
| 4-OCF₂H | 4-Cl | H | 4-CO₂Me | CHO | |
| 4-OCF₃ | 4-Cl | H | 4-CO₂Me | CHO | |
| 4-CF₃ | 4-Cl | H | 4-CO₂Me | CO₂Et | |
| 4-Cl | 4-Cl | H | 4-CO₂Me | CO₂Et | |
| 4-OCF₂H | 4-Cl | H | 4-CO₂Me | CO₂Et | |
| 4-OCF₃ | 4-Cl | H | 4-CO₂Me | CO₂Et | |
| 4-CF₃ | 4-Cl | H | 4-CO₂Me | C(O)Et | |
| 4-Cl | 4-Cl | H | 4-CO₂Me | C(O)Et | |
| 4-OCF₂H | 4-Cl | H | 4-CO₂Me | C(O)Et | |
| 4-OCF₃ | 4-Cl | H | 4-CO₂Me | C(O)Et | |
| 4-CF₃ | 4-Cl | H | 4-CO₂Me | C(O)CH₂Cl | |
| 4-Cl | 4-Cl | H | 4-CO₂Me | C(O)CH₂Cl | |
| 4-OCF₂H | 4-Cl | H | 4-CO₂Me | C(O)CH₂Cl | |
| 4-OCF₃ | 4-Cl | H | 4-CO₂Me | C(O)CH₂Cl | |
| 4-CF₃ | 4-Cl | H | 4-CO₂Me | SMe | |
| 4-Cl | 4-Cl | H | 4-CO₂Me | SMe | |
| 4-CF₃ | 4-Cl | H | 4-CO₂Me | SPh | |
| 4-Cl | 4-Cl | H | 4-CO₂Me | SPh | |
| 4-CF₃ | 4-Cl | H | 4-CO₂Me | n-Bu | |
| 4-CF₃ | 4-F | H | 4-CO₂Et | Me | |
| 4-CF₃ | 4-F | H | 4-CONMe₂ | Me | |
| 4-CF₃ | 4-F | H | 4-CHO | Me | |
| 4-CF₃ | 4-F | H | 4-C(O)Me | Me | |
| 4-CF₃ | 4-F | H | 4-SO₂NMe | CHO | |
| 4-CF₃ | 4-F | H | 4-CO₂Et | CHO | |
| 4-CF₃ | 4-F | H | 4-CHO | CHO | |
| 4-CF₃ | 4-F | H | 4-C(O)Me | CO₂Me | |
| 4-CF₃ | 4-F | H | 4-SO₂NMe₂ | CO₂Me | |
| 4-CF₃ | 4-F | H | 4-CO₂Et | CO₂Me | |
| 4-CF₃ | 4-F | H | 4-CONMe₂ | CO₂Me | |
| 4-CF₃ | 4-F | H | 4-CHO | SMe | |
| 4-CF₃ | 4-F | H | 4-C(O)Me | SMe | |
| 4-CF₃ | 4-F | H | 4-SO₂NMe₂ | SMe | |
| 4-CF₃ | H | H | 4-CO₂Et | SMe | |

[1] R₁ or R₂ substitutents designated as disubstituted with two open termini are bound to phenyl to form a bicyclic ring such that the first numerical designation defines the position of the first listed terminus and the second numerical designation defines the position of the other terminus.

TABLE 2

| R₁ | R₂ | R₃ | R₅ | Y | Phys. Prop. |
|---|---|---|---|---|---|
| 4-CF₃ | 4-Cl | H | 4-CO₂Me | H | semi-solid |
| 4-Cl | 4-Cl | H | 4-CO₂Me | H | |
| 4-Br | 4-Cl | H | 4-CO₂Me | H | |
| 4-OCF₂H | 4-F | H | 4-CO₂Me | H | |
| 4-OCF₃ | 4-F | H | 4-CO₂Me | H | |
| 4-F | 4-F | H | 4-CO₂Me | H | |
| 3,4-OCF₂CF₂[1] | 4-OCF₂H | H | 4-SO₂NMe₂ | H | |
| 4-CO₂-i-C₃H₇ | 4-OCF₂H | H | 4-SO₂NMe₂ | H | |
| 4-CF₃ | 4-OCF₂H | H | 4-SO₂NMe₂ | H | |
| 4-Cl | 4-OCF₃ | H | 4-SO₂NMe₂ | H | |
| 4-Br | 4-OCF₃ | H | 4-SO₂NMe₂ | H | |
| 4-OCF₂H | 4-OCF₃ | H | 4-SO₂NMe₂ | H | |
| 4-OCF₃ | 4-Br | H | 4-C(O)Me | H | |
| 4-F | 4-Br | H | 4-C(O)Me | H | |
| 3,4-OCF₂CF₂[1] | 4-Br | H | 4-C(O)Me | H | |
| 4-CO₂-i-C₃H₇ | 4-CF₃ | H | 4-C(O)Me | H | |
| 4-CF₃ | 4-CF₃ | H | 4-C(O)Me | H | |
| 4-Cl | 4-CF₃ | H | 4-C(O)Me | H | |
| 4-Br | 4-NMe₂ | H | 4-CO₂Me | H | |
| 4-OCF₂H | 4-NO₂ | H | 4-CO₂Me | H | |
| 4-OCF₃ | 4-OMe | H | 4-CO₂Me | H | |
| 4-CF₃ | 4-Br | H | 4-CO₂Me | H | m.p. 188 to 189.5° C. |
| 4-CF₃ | 4-CO₂Me | H | 4-CO₂Me | H | m.p. 173 to |

TABLE 2-continued

| $R_1$ | $R_2$ | $R_3$ | $R_5$ | Y | Phys. Prop. |
|---|---|---|---|---|---|
| | | | | | 175° C. |
| 4-F | 4-Cl | H | 4-CO$_2$Me | H | |
| 4-CF$_3$ | 4-Cl | H | 4-CONMe$_2$ | H | |
| 4-Cl | 4-Cl | H | 4-CONMe$_2$ | H | |
| 4-Br | 4-Cl | H | 4-CONMe$_2$ | H | |
| 4-OCF$_2$H | 4-F | H | 4-CONMe$_2$ | H | |
| 4-OCF$_3$ | 4-F | H | 4-CONMe$_2$ | H | |
| 4-F | 4-F | H | 4-CONMe$_2$ | H | |
| 3,4-OCF$_2$CF$_2$[1] | 4-OCF$_2$H | H | 4-CHO | H | |
| 4-CO$_2$-i-C$_3$H$_7$ | 3-OCF$_2$H | H | 4-CHO | H | |
| 4-CF$_3$ | 4-OCF$_2$H | H | 4-CHO | H | |
| 4-Cl | 4-OCF$_3$ | H | 4-CHO | H | |
| 4-Br | 4-OCF$_3$ | H | 4-CHO | H | |
| 4-OCF$_2$H | 4-OCF$_3$ | H | 4-CO$_2$H | H | |
| 4-OCF$_3$ | 4-Br | H | 4-CO$_2$H | H | |
| 4-F | 4-Br | H | 4-CO$_2$H | H | |
| 3,4-OCF$_2$CF$_2$[1] | 4-Br | H | 4-CO$_2$H | H | |
| 4-CO$_2$-i-C$_3$H$_7$ | 4-CF$_3$ | H | 4-CO$_2$H | H | |
| 4-Cl | 4-CF$_3$ | H | 4-CO$_2$Et | H | m.p. 170 to 173° C. |
| 4-Cl | 4-CF$_3$ | H | 4-CO$_2$Et | H | |
| 4-Br | 4-NMe$_2$ | H | 4-CO$_2$Et | H | |
| 4-OCF$_2$H | 3-NO$_2$ | H | 4-CO$_2$Et | H | |
| 4-OCF$_3$ | 4-OMe | H | 4-CO$_2$Et | H | |
| 4-F | 4-Cl | H | 4-CO$_2$Et | H | |

TABLE 3

| $R_1$ | $R_2$ | $R_3$ | $R_5$ | $R_6$ | $R_7$ | Phys. Prop. |
|---|---|---|---|---|---|---|
| 4-CF$_3$ | 4-Cl | H | 4-CO$_2$Me | Me | H | m.p. 92 to 98 |
| 4-Cl | 4-Cl | H | 4-CO$_2$Me | Me | H | m.p. 90 to 95 |
| 4-Br | 4-Cl | H | 4-CO$_2$Me | Me | H | m.p. 82 to 86 |
| 4-OCF$_2$H | 4-Cl | H | 4-CO$_2$Me | Me | H | |
| 4-OCF$_3$ | 4-Cl | H | 4-CO$_2$Me | Me | H | |
| 4-CF$_3$ | 4-Cl | H | 4-C(O)Me | Me | H | |
| 4-Cl | 4-Cl | H | 4-C(O)Me | Me | H | |
| 4-Br | 4-Cl | H | 4-C(O)Me | Me | H | |
| 4-OCF$_2$H | 4-Cl | H | 4-C(O)Me | Me | H | |
| 4-OCF$_3$ | 4-Cl | H | 4-C(O)Me | Me | H | |
| 4-CF$_3$ | 4-F | H | 4-CO$_2$Me | Me | H | |
| 4-Cl | 4-F | H | 4-CO$_2$Me | Me | H | |
| 4-Br | 4-F | H | 4-CO$_2$Me | Me | H | |
| 4-OCF$_2$H | 4-F | H | 4-CO$_2$Me | Me | H | |
| 4-OCF$_3$ | 4-F | H | 4-CO$_2$Me | Me | H | |
| 4-CF$_3$ | 4-F | H | 4-CONMe$_2$ | Me | H | |
| 4-Br | 4-F | H | 4-CONMe$_2$ | Me | H | |
| 4-OCF$_2$H | 4-F | H | 4-CONMe$_2$ | Me | H | |
| 4-OCF$_3$ | 4-F | H | 4-CONMe$_2$ | Me | H | |
| 4-CF$_3$ | 4-Cl | H | 4-CO$_2$Me | Me | Me | |
| 4-Cl | 4-Cl | H | 4-CO$_2$Me | Me | Me | |
| 4-Br | 4-Cl | H | 4-CO$_2$Me | Me | Me | |
| 4-OCF$_2$H | 4-Cl | H | 4-CO$_2$Me | Me | Me | |
| 4-OCF$_3$ | 4-Cl | H | 4-CO$_2$Me | Me | Me | |
| 4-CF$_3$ | 4-Cl | H | 4-SO$_2$NMe$_2$ | Me | Me | |
| 4-Cl | 4-Cl | H | 4-SO$_2$NMe$_2$ | Me | Me | |
| 4-Br | 4-Cl | H | 4-SO$_2$NMe$_2$ | Me | Me | |
| 4-OCF$_2$H | 4-Cl | H | 4-SO$_2$NMe$_2$ | Me | Me | |
| 4-OCF$_3$ | 4-Cl | H | 4-SO$_2$NMe$_2$ | Me | Me | |
| 4-CF$_3$ | 4-F | H | 4-CO$_2$Me | Me | Me | |
| 4-Cl | 4-F | H | 4-CO$_2$Me | Me | Me | |
| 4-Br | 4-F | H | 4-CO$_2$Me | Me | Me | |
| 4-OCF$_2$H | 4-F | H | 4-CO$_2$Me | Me | Me | |
| 4-OCF$_3$ | 4-F | H | 4-CO$_2$Me | Me | Me | |
| 4-CF$_3$ | 4-F | H | 4-CO$_2$H | Me | Me | |
| 4-Cl | 4-F | H | 4-CO$_2$H | Me | Me | |
| 4-Br | 4-F | H | 4-CO$_2$H | Me | Me | |
| 4-OCF$_2$H | 4-F | H | 4-CO$_2$H | Me | Me | |
| 4-OCF$_3$ | 4-F | H | 4-CO$_2$H | Me | Me | |
| 4-CF$_3$ | 4-Cl | H | 4-CO$_2$Me | Et | H | |
| 4-CF$_3$ | 4-F | H | 4-CO$_2$Me | Et | H | |
| 4-CF$_3$ | 4-OCF$_2$H | H | 4-CO$_2$Me | Et | H | |
| 4-CF$_3$ | 4-Cl | H | 4-CO$_2$Et | Et | H | |
| 4-CF$_3$ | 4-F | H | 4-CO$_2$Et | Et | H | |
| 4-CF$_3$ | 4-OCF$_2$H | H | 4-CO$_2$Et | Et | H | |
| 4-CF$_3$ | 4-Cl | H | 4-CO$_2$Me | i-Pr | H | |
| 4-CF$_3$ | 4-F | H | 4-CO$_2$Me | i-Pr | H | |
| 4-CF$_3$ | 4-OCF$_2$H | H | 4-CO$_2$Me | i-Pr | H | |
| 4-CF$_3$ | 4-Cl | H | 4-CO$_2$Et | i-Pr | H | |
| 4-CF$_3$ | 4-F | H | 4-CO$_2$Et | n-Pr | H | |

TABLE 3-continued

| $R_1$ | $R_2$ | $R_3$ | $R_5$ | $R_6$ | $R_7$ | Phys. Prop. |
|---|---|---|---|---|---|---|
| 4-CF$_3$ | 4-OCF$_2$H | H | 4-CO$_2$Et | n-Pr | H | |
| 4-CF$_3$ | 4-Cl | H | 4-CO$_2$Me | n-Pr | H | |
| 4-CF$_3$ | 4-F | H | 4-CO$_2$Me | n-Pr | H | |
| 4-CF$_3$ | 4-OCF$_2$H | H | 4-CO$_2$Me | n-Pr | H | |
| 4-CF$_3$ | 4-Cl | H | 4-CO$_2$Et | n-Bu | H | |
| 4-CF$_3$ | 4-F | H | 4-CO$_2$Et | n-Bu | H | |
| 4-CF$_3$ | 4-OCF$_2$H | H | 4-CO$_2$Et | n-Bu | H | |
| 4-CF$_3$ | 4-Cl | H | 4-CO$_2$Me | n-Bu | H | |
| 4-CF$_3$ | 4-F | H | 4-CO$_2$Me | n-Bu | H | |

Formulation and Use

The compounds of this invention will generally be used in formulation with a carrier comprising a liquid or solid diluent or an organic solvent. Useful formulations of the compounds of Formula I can be prepared in conventional ways. They include dusts, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual:, MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147 and following, and "Perry's Chemical Engineer's Handbook", 4th Ed., McGraw-Hill, New York, 1963, pages 8 to 59 and following.

Examples of useful formulations of compounds of the present invention are as follows:

EXAMPLE 2

Emulsifiable Concentrate

| | |
|---|---|
| N,3-bis[4-(trifluoromethyl)phenyl]-4-[4-(dimethylamino)-sulfonyl]phenyl]-4,5-dihydro-1H-pyrazole-1-carboxamide | 10% |
| blend of oil soluble sulfonates and polyoxyethylene ethers | 4% |
| isophorone | 86% |

The ingredients are combined and stirred with gentle warming to speed solution. A fine screen filter is included in packaging operation to insure the absence of any extraneous undissolved material in the product.

EXAMPLE 3

Wettable Powder

| | |
|---|---|
| methyl 4-[3-(4-chlorophenyl)-4,5-dihydro-1-[[4-(trifluoromethyl)phenylamino]carbonyl]-1H-pyrazol-4-yl]benzoate | 80% |
| sodium alkylnaphthalenesulfonate | 2% |
| sodim ligninsulfonate | 2% |
| synthetic amorphous silica | 3% |
| kaolinite | 3% |

The active ingredient is blended with the inert materials in a blender. After grinding in a hammermill, the material is reblended and sifted through a U.S.S. 50 mesh screen and packaged.

EXAMPLE 4

Dust

| | |
|---|---|
| wettable powder of Example 2 | 5% |
| pyrophyllite (powder) | 95% |

The wettable powder and the pyrophyllite diluent are thoroughly blended and then packaged. The product is suitable for use as a dust.

EXAMPLE 5

Granule

| | |
|---|---|
| methyl 4-[3-(4-chlorophenyl)-4,5-dihydro-1-[[4-(trifluoromethyl)phenylamino]carbonyl]-1H-pyrazol-4-yl]benzoate | 10% |
| attapulgite granules (low volative matter, 0.71/0.30 mm; U.S.S. No. 25-50 sieves) | 90% |

The active ingredient is dissolved in a suitable solvent and sprayed onto dedusted attapulgite granules in a double cone blender. The granules are warmed to drive off solvent, cooled and packaged.

EXAMPLE 6

Granule

| | |
|---|---|
| wettable powder of Example 2 | 15% |
| gypsum | 69% |
| potassium sulfate | 16% |

The ingredients are blended in a rotating mixer and water is sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 12% active ingredient.

EXAMPLE 7

Solution

| | |
|---|---|
| methyl 4-[3-(4-chlorophenyl)-4,5-dihydro-1-[[4-(trifluoromethyl)phenylamino]carbonyl]-1H-pyrazol-4-yl]benzoate | 15% |
| 4-butyrolactone | 85% |

The ingredients are combined and stirred to produce a solution suitable for direct, low volume application.

EXAMPLE 8

Oil Suspension

| | |
|---|---|
| methyl 4-3-(4-chlorophenyl)-4,5-dihydro-1-[[4-(trifluoromethyl)phenylamino]carbonyl]-1H-pyrazol-4-yl]benzoate | 25% |
| polyoxyethylene sorbitol hexaoleate | 5% |
| highly aliphatic hydrocarbon oil | 70% |

The ingredients are ground together in a sand mill until the solid particles have been reduced to under 5 microns. The resulting thick suspension may be applied directly, but preferable after being extended with oils or emulsified in water.

EXAMPLE 9

Wettable Powder

| | |
|---|---|
| methyl 4-[3-(4-chlorophenyl)-4,5-dihydro-1-[[4-(trifluoromethyl)phenylamino]carbonyl]-1H-pyrazol-4-yl]benzoate | 20% |
| sodium alkylnaphthalenesulfonate | 4% |
| sodium lignosulfonate | 4% |
| low viscosity methyl cellulose | 3% |
| attapulgite | 69% |

The active ingredient is blended with the inert materials in a blender. After griding in a hammermill to produce particles essentially all below 100 microns, the material is reblended and sifted through a U.S.S. 50 mesh screen and packaged.

Compounds of Formula I can also be mixed with one or more other insecticides, fungicides, nematocides, bactericides, acaricides, or other biologically active compounds to form a multicomponent pesticide giving an even broader spectrum of effective agricultural protection. Examples of other agricultural protectants with which compounds of the present invention can be mixed or formulated are:

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-a-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with a-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl O-p-nitrophenyl phenylphosphonothioate (EPN)
(S)-a-cyano-m-phenoxybenzyl(1R,3R)-3-(2,2-dibromovinyl)-2,2-dimethylcyclopropanecarboxylate (deltamethrin)
Methyl N',N'-dimethyl-N-[(methylcarbamoyl)oxy]-1-thiooxamimidate (oxamyl)
cyano(3-phenoxyphenyl)-methyl-4-chloro-a-(1-methylethyl)benzeneacetate (fenvalerate)
(3-phenoxyphenyl)methyl(+)-cis,trans-3-(2,2-dichloroethenyl)-2,2-dimethylcyclopropanecarboxylate (permethrin)
a-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid,
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotophos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides methyl 2-benzimidazolecarbamate (carbendazim)
tetramethylthiuran disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides

S-methyl 1-(dimethylcarbamoyl)-N-(methylcarbamoyloxy)-thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Bactericides tribasic copper sulfate
streptomycin sulfate.

Acaricides senecioic acid, ester with 2-sec-butyl-4,6-dinitrophenol (binapacryl)
6-methyl-1,3-dithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
bisclofentezin.

Biological

Bacillus thuringiensis
Avermectin B.

Utility

The compounds of the present invention exhibit activity against a wide spectrum of foliar and soil inhabiting insects. Those skilled in the art will recognize that not all compounds will be equally effective against all insects, but compounds of this invention display control of many of the economically important pest species of the insect orders Lepidoptera, Homoptera, and Coleoptera among many others. The specific species for which control is exemplified below are: fall armyworm, *Spodoptera frugiperda*; boll weevil, *Anthonomus grandis*; European corn borer, *Ostrinia nubilalis*; southern corn rootworm, *Diabrotica undecimpunctata howardi*; aster leafhopper, *Macrosteles fascifrons*. The pest control afforded by the compounds of the present invention is not limited, however, to these species.

Application

Insects are controlled and agricultural crops are Protected by applying one or more of the Formula I compounds of this invention, in an effective amount, to the locus of infestation, to the area to be protected (the environment of the pests), or directly on the pests to be controlled. A preferred method of application is by spraying with spray equipment that distributes the compound on the foliage, in the soil, or to the plant part that is infested or needs to be protected. Alternatively, granular formulations of these compounds can be applied to soil or foliage or, optionally, incorporated into the soil. Either aerial or ground application can be used.

The pyrazoline compound(s) of this invention can be applied in its (their) pure state, but most often application will be of a formulation comprising one or more compounds of this invention, in an agriculturally suitable carrier or diluent. A most preferred method of application involves spraying a water dispersion or refined oil solution of the compounds.

The rate of application of the Formula I compounds required for effective control will depend on such factors as the insect species population size, the pest's life stage, insect size, its location, the host crop, the host stage, time of year of application, placement of the insecticide, temperature conditions, and others. In general, application rates of 0.05 to 2 kg of active ingredient per hectare are sufficient to provide effective control in large scale field operations under normal circumstances, but as little as 0.01 kg/hectare may be sufficient or as much as 8 kg/hectare may be required, depending upon the factors listed above.

Examples 10 to 15 demonstrate the control efficacy of compounds of Formula I on specific insect pests. Compounds 1 through 115 in these tests are described in Table 4. In each of Compounds 1 to 115, $R_6$, $R_7$ and Y are hydrogen and X is oxygen with the following exceptions: in compound 81, Y is methyl and in compounds 104 to 106, $R_6$ is methyl.

TABLE 4

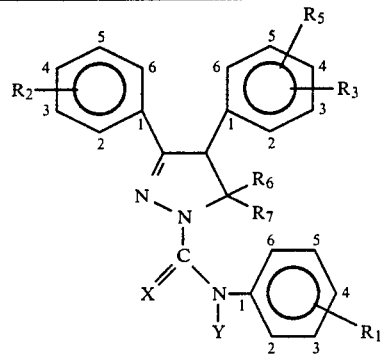

| CMPD | $R_1$ | $R_2$ | $R_3$ | $R_5$ |
|---|---|---|---|---|
| 1 | 4-$CF_3$ | 4-Cl | H | 4-$CO_2Me$ |
| 2 | 4-Cl | 4-Cl | H | 4-$CO_2Me$ |
| 3 | 4-$CF_3$ | 4-F | H | 4-$CO_2Me$ |
| 4 | 4-Cl | 4-F | H | 4-$CO_2Me$ |
| 5 | 4-$CF_3$ | 4-$CF_3$ | H | 4-$SO_2NMe_2$ |
| 6 | 4-Cl | 4-$CF_3$ | H | 4-$SO_2NMe_2$ |
| 7 | 4-SMe | 4-$CF_3$ | H | 4-$SO_2NMe_2$ |
| 8 | 4-$CF_3$ | H | H | 4-$CO_2Me$ |
| 9 | 4-Cl | H | H | 4-$CO_2Me$ |
| 10 | 4-Br | H | H | 4-$CO_2Me$ |
| 11 | 4-Br | 4-Cl | H | 4-$CO_2Me$ |
| 12 | 4-SMe | 4-Cl | H | 4-$CO_2Me$ |
| 13 | 4-$CF_3$ | 4-Cl | H | 4-$CO_2Et$ |
| 14 | 4-Cl | 4-Cl | H | 4-$CO_2Et$ |
| 15 | 4-Br | 4-Cl | H | 4-$CO_2Et$ |
| 16 | 4-SMe | 4-Cl | H | 4-$CO_2Et$ |
| 17 | 4-$CF_3$ | 4-Cl | H | 4-$CO_2$-i-Pr |
| 18 | 4-Cl | 4-Cl | H | 4-$CO_2$-i-Pr |
| 19 | 4-Br | 4-Cl | H | 4-$CO_2$-i-Pr |
| 20 | 4-SMe | 4-Cl | H | 4-$CO_2$-i-Pr |
| 21 | 4-$CF_3$ | 4-$CF_3$ | H | 4-$CO_2Me$ |
| 22 | 4-$CF_3$ | 4-Cl | H | 4-$CO_2Me$ |
| 23 | 4-$CF_3$ | 4-Cl | H | 4-$CONMe_2$ |
| 24 | 4-Cl | 4-Cl | H | 4-$CONMe_2$ |
| 25 | 4-Br | 4-Cl | H | 4-$CONMe_2$ |
| 26 | 4-$CF_3$ | 4-Cl | H | 4-CONHMe |
| 27 | 4-Cl | 4-Cl | H | 4-CONHMe |
| 28 | 3,4-di-Cl | 4-Cl | H | 4-CONHMe |
| 29 | 4-F | 4-Cl | H | 4-CONHMe |
| 30 | 4-$CF_3$ | 4-CN | H | 4-$CO_2Me$ |
| 31 | 4-Cl | 4-CN | H | 4-$CO_2Me$ |
| 32 | 3,4-di-Cl | 4-CN | H | 4-$CO_2Me$ |
| 33 | 4-$CF_3$ | 3-Cl | H | 4-$CO_2Me$ |
| 34 | 4-Cl | 3-Cl | H | 4-$CO_2Me$ |
| 35 | 3,4-di-Cl | 3-Cl | H | 4-$CO_2Me$ |
| 36 | 4-$CF_3$ | 4-$CO_2Me$ | H | 4-$CO_2Me$ |
| 37 | 4-Cl | 4-$CO_2Me$ | H | 4-$CO_2Me$ |
| 38 | 4-$CO_2Et$ | 4-$CO_2Me$ | H | 4-$CO_2Me$ |
| 39 | 4-$CF_3$ | 4-$OCH_2C(Cl)=CH_2$ | H | 4-$CO_2Me$ |
| 40 | 4-$CF_3$ | 4-OPh | H | 4-$CO_2Me$ |
| 41 | 4-Cl | 4-OPh | H | 4-$CO_2Me$ |
| 42 | 4-Br | 4-OPh | H | 4-$CO_2Me$ |
| 43 | 4-$CF_3$ | 3,4-di-Cl | H | 4-$CO_2Me$ |
| 44 | 4-Cl | 3,4-di-Cl | H | 4-$CO_2Me$ |
| 45 | 4-Br | 3,4-di-Cl | H | 4-$CO_2Me$ |

TABLE 4-continued

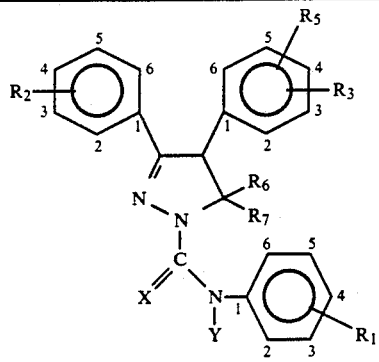

| CMPD | R₁ | R₂ | R₃ | R₅ |
|------|-----|-----|-----|-----|
| 46 | 3,4-di-Cl | 3,4-di-Cl | H | 4-CO₂Me |
| 47 | 3-CF₃ | 4-CO₂Me | H | 4-CO₂Me |
| 48 | 4-OMe | 4-CO₂Me | H | 4-CO₂Me |
| 49 | 4-Cl | 4-Br | H | 4-CO₂Me |
| 50 | 4-Br | 4-Br | H | 4-CO₂Me |
| 51 | 4-OMe | 4-Br | H | 4-CO₂Me |
| 52 | 4-CF₃ | 4-Br | H | 4-CO₂Me |
| 53 | 4-CF₃ | 4-Cl | H | 3-CO₂Me |
| 54 | 4-Cl | 4-Cl | H | 3-CO₂Me |
| 55 | 4-Br | 4-Cl | H | 3-CO₂Me |
| 56 | 4-CO₂Et | 4-Cl | H | 3-CO₂Me |
| 57 | 4-CF₃ | 4-Cl | H | 4-CO₂CH₂CF₃ |
| 58 | 4-Cl | 4-Cl | H | 4-CO₂CH₂CF₃ |
| 59 | 4-Br | 4-Cl | H | 4-CO₂CH₂CF₃ |
| 60 | 4-CF₃ | 4-Cl | H | 4-SO₂NHMe |
| 61 | 4-Cl | 4-Cl | H | 4-SO₂NHMe |
| 62 | 4-CF₃ | 4-Cl | H | 4-SO₂NMe₂ |
| 63 | 4-Cl | 4-Cl | H | 4-SO₂NMe₂ |
| 64 | 4-CF₃ | 4-Cl | H | 4-C(O)Me |
| 65 | 4-Cl | 4-Cl | H | 4-C(O)Me |
| 66 | 4-CF₃ | 4-OCF₃ | H | 4-CO₂Me |
| 67 | 4-Cl | 4-OCF₃ | H | 4-CO₂Me |
| 68 | 4-Br | 4-OCF₃ | H | 4-CO₂Me |
| 69 | 4-CF₃ | 4-SMe | H | 4-CO₂Me |
| 70 | 4-Cl | 4-SMe | H | 4-CO₂Me |
| 71 | 4-Br | 4-SMe | H | 4-CO₂Me |
| 72 | 4-SMe | 4-SMe | H | 4-CO₂Me |
| 73 | 3-Cl-4-F | 4-SMe | H | 4-CO₂Me |
| 74 | 4-CF₃ | 4-SO₂Me | H | 4-CO₂Me |
| 75 | 4-Cl | 4-SO₂Me | H | 4-CO₂Me |
| 76 | 4-Br | 4-SO₂Me | H | 4-CO₂Me |
| 77 | 4-CF₃ | 4-NMe₂ | H | 4-CO₂Me |
| 78 | 4-Cl | 4-NMe₂ | H | 4-CO₂Me |
| 79 | 4-Br | 4-NMe₂ | H | 4-CO₂Me |
| 80 | 3-Cl-4-F | 4-NMe₂ | H | 4-CO₂Me |
| 81 | 4-CF₃ | 4-Cl | H | 4-CO₂Me |
| 82 | 4-CO₂Et | 4-Cl | H | 4-CO₂Me |
| 83 | 3-NO₂-4-Cl | 4-Cl | H | 4-CO₂Me |
| 84 | 2-OMe-3-Cl | 4-Cl | H | 4-CO₂Me |
| 85 | 3-Cl-4-F | 4-Cl | H | 4-CO₂Me |
| 86 | 4-Cl-3-CF₃ | 4-Cl | H | 4-CO₂Me |
| 87 | 3,4-di-Cl | 4-Cl | H | 4-CO₂Me |
| 88 | 4-CF₃ | 3-Cl | H | 4-CO₂CH₂C≡CH |
| 89 | 4-Cl | 4-Cl | H | 4-CO₂CH₂C≡CH |
| 90 | 4-Br | 4-Cl | H | 4-CO₂CH₂C≡CH |
| 91 | 4-CF₃ | 4-CF₂HO | H | 4-CO₂Me |
| 92 | 4-CF₃ | 3,4-di-F | H | 4-CO₂Me |
| 93 | 4-Cl | 3,4-di-F | H | 4-CO₂Me |
| 94 | 4-Br | 3,4-di-F | H | 4-CO₂Me |
| 95 | 4-CO₂Et | 3,4-di-F | H | 4-CO₂Me |
| 96 | 3-CF₃-4-Cl | 3,4-di-F | H | 4-CO₂Me |
| 97 | 4-CF₃ | 4-Cl | 4-Cl | 3-CO₂Me |
| 98 | 4-Cl | 4-Cl | 4-Cl | 3-CO₂Me |
| 99 | 4-Br | 4-Cl | 4-Cl | 3-CO₂Me |
| 100 | 4-F | 4-Cl | 4-Cl | 3-CO₂Me |
| 101 | 3-CF₃-4-Cl | 4-Cl | 4-Cl | 3-CO₂Me |
| 102 | 3-CF₃-4-Cl | 4-Cl | H | 4-CO₂Et |
| 103 | 3-Cl-4-F | 4-Cl | H | 4-CO₂Et |
| 104 | 4-CF₃ | 4-Cl | H | 4-CO₂Me |
| 105 | 4-Cl | 4-Cl | H | 4-CO₂Me |
| 106 | 4-Br | 4-Cl | H | 4-CO₂Me |
| 107 | 4-Cl | 4-OH | H | 4-CO₂Me |
| 108 | 4-Br | 4-OH | H | 4-CO₂Me |

TABLE 4-continued

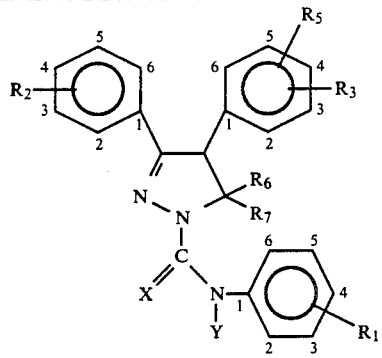

| CMPD | $R_1$ | $R_2$ | $R_3$ | $R_5$ |
|---|---|---|---|---|
| 109 | 4-$CF_3$ | 4-OH | H | 4-$CO_2Me$ |
| 110 | 4-$CF_3$ | 4-OMe | H | 4-$CO_2Me$ |
| 111 | 4-Br | 4-OMe | H | 4-$CO_2Me$ |
| 112 | 4-$CF_3$ | 4-Cl | H | 4-$CO_2Et$ |
| 113 | 4-$CF_3$ | 4-$CO_2Me$ | H | 4-$CO_2Me$ |
| 114 | 4-$CF_3$ | 4-Br | H | 4-$CO_2Me$ |
| 115 | 4-$CF_3$ | 4-Cl | H | 4-$CO_2Me$ |

EXAMPLE 10

Fall Armyworm

A test unit consisted of an 8-ounce plastic cup containing a layer of wheat germ diet, approximately 0.5 cm thick infested with ten third-instar larvae of fall armyworm (*Spodoptera frugiperda*). Solutions of each of the above-listed test compounds were made by combining the compound in an acetone/distilled water 75/25 solvent and then sprayed onto the cups; a single solution per cup replicated three times. Spraying was accomplished by passing the cups, on a conveyor belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time mortality readings were taken. Tested compounds which killed 80% or more of the larvae are listed below:

| | | | | | |
|---|---|---|---|---|---|
| 1 | 16 | 30 | 46 | 59 | 86 |
| 2 | 17 | 31 | 49 | 60 | 91 |
| 3 | 18 | 32 | 50 | 62 | 92 |
| 4 | 19 | 33 | 52 | 66 | 93 |
| 8 | 21 | 34 | 53 | 67 | 104 |
| 10 | 22 | 41 | 54 | 68 | 105 |
| 11 | 23 | 42 | 55 | 79 | 106 |
| 13 | 26 | 43 | 56 | 81 | 114 |
| 14 | 27 | 44 | 57 | 82 | 115 |
| 15 | 28 | 45 | 58 | 85 | |

EXAMPLE 11

Tobacco Budworm

The test procedure of Example 10 was repeated for efficacy against third-instar larvae of the tobacco budworm (*Heliothis virescens*) except that mortality was assessed at 48 hours. Tested compounds which killed 80% or more of the larvae are listed below:

| | | | | |
|---|---|---|---|---|
| 1 | 17 | 32 | 58 | 104 |
| 2 | 18 | 33 | 59 | 106 |
| 3 | 19 | 44 | 62 | 112 |
| 4 | 21 | 45 | 66 | 114 |
| 8 | 22 | 46 | 67 | 115 |
| 11 | 23 | 49 | 81 | |
| 13 | 26 | 50 | 85 | |
| 14 | 28 | 52 | 86 | |
| 15 | 30 | 53 | 91 | |
| 16 | 31 | 57 | 92 | |

EXAMPLE 12

European Corn Borer

A test unit consisted of an 8-ounce plastic cup containing a one-inch square of wheat germ/soyflour diet infested with five third-instar larvae of the European corn borer (*Ostrinia nubilalis*). Test units were sprayed as described in Example 10. The cups were then covered and held at 27° C. and 50% relative himidity for 48 hours, after which time mortality readings were taken. Tested compounds which killed or more of the larvae are listed below:

| | |
|---|---|
| 1 | 21 |
| 2 | 22 |
| 3 | 26 |
| 4 | 30 |
| 11 | 33 |
| 12 | 50 |
| 13 | 52 |
| 14 | |
| 15 | |

EXAMPLE 13

Southern Corn Rootworm

A test unit consisted of an 8-ounce plastic cup containing 1 sprouted corn seed. The test units were sprayed as described in Example 10. After the treated cup had dried it was infested with five third-instar larvae of the Southern corn rootworm (*Diabrotica undecimpunctata howardi*) and replicated three times. A moistened dental wick was inserted into each cup to prevent drying and the cups were covered. The cups were then held at 27° C. and 50% humidity for 48 hours, after which time mortality readings were taken. Tested compounds which killed 80% or more of the larvae are listed below:

| |
|---|
| 8 |
| 10 |
| 28 |
| 55 |
| 56 |
| 58 |
| 91 |
| 93 |

EXAMPLE 14

Boll Weevil

The test unit consisted of five adult boll weevils (*Anthonomus grandis*) in a 9-ounce cup. The test procedure employed was the same as in Example 10. Mortality readings were taken 48 hours after treatment. Tested compounds which killed 80% or more of the adults are listed below:

| | |
|---|---|
| 1 | 15 |
| 2 | 21 |
| 3 | 22 |
| 4 | 26 |
| 12 | 30 |
| 13 | 33 |
| 14 | 52 |

EXAMPLE 15

Aster Leafhopper

A test unit was a 12-ounce cup containing oat (*Avena sativa*) seedlings in a 1-inch layer of sterilized soil. Test units were sprayed as described in Example 10. After the treated oats had dried between 10 and 15 adult aster leafhoppers (*Mascrosteles fascifrons*) were aspirated into each of the covered cups. The cups were held at 27° C. and 50% relative humidity for 48 hours, and evaluated for mortality. Tested compounds which killed 80% or more of the insects are 22, 49, 50, 58 and 91.

What is claimed is:

1. A compound of the formula

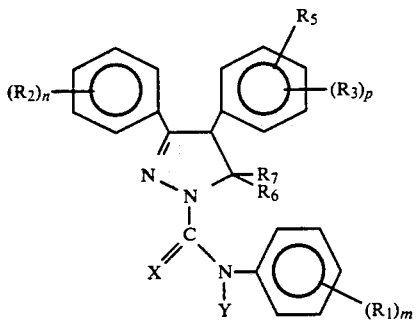

wherein $R_1$, $R_2$ and $R_3$ are independently selected from $R_8$, halogen, CN, $N_3$, SCN, $NO_2$, $OR_8$, $SR_8$, $S(O)R_8$, $S(O)_2R_8$, $OC(O)R_8$, $OS(O)_2R_8$, $C(O)OR_8$, $C(O)R_8$, $C(O)NR_8R_9$, $S(O)_2NR_8R_9$, $NR_8R_9$, $NR_9C(O)R_8$, $OC(O)NHR_8$, $NR_9C(O)NHR_8$ and $NR_9S(O)_2R_8$, or when m, n or p is 2, $R_1$, $R_2$ or $R_3$ can be taken together as $OCH_2O$, $OCH_2CH_2O$ or $CH_2CH_2O$, to form a 5 or 6 membered ring, each of which can be substituted with 1 to 4 halogen atoms or 1 to 2 methyl groups;

$R_5$ is selected from $C(O)OR_{10}$, $C(O)R_{10}$, $C(O)NR_{10}R_{11}$, $C(S)SR_{10}$, $C(S)NR_{10}R_{11}$ and $S(O)_2NR_{10}R_{11}$;

$R_6$ is H or $C_1$ to $C_4$ alkyl;

$R_7$ is H or $CH_3$;

$R_8$ and $R_{10}$ are independently selected from H, $C_1$ to $C_4$ alkyl, $C_3$ to $C_4$ alkenyl, $C_3$ to $C_4$ alkynyl, $C_1$ to $C_4$ haloalkyl, $C_3$ to $C_4$ haloalkenyl, $C_1$ to $C_4$ alkyl substituted with CN, $C(O)OCH_3$, $C(O)OCH_2CH_3$, $OCH_3$, $OCH_2CH_3$, $SCH_3$, $SCH_2CH_3$ and $NO_2$, and phenyl or benzyl, either optionally substituted with W, or $R_8$ and $R_9$ can be taken together as $(CH_2)_4$, $(CH_2)_5$ or $CH_2CH_2OCH_2CH_2$;

$R_9$ and $R_{11}$ are independently selected from H, $C_1$ to $C_4$ alkyl, $C_3$ to $C_4$ alkenyl, $C_3$ to $C_4$ alkynyl, and $C_1$ to $C_4$ haloalkyl, or $R_{10}$ and $R_{11}$ can be taken together as $(CH_2)_4$, $(CH_2)_5$ or $CH_2CH_2OCH_2CH_2$;

m and n are independently 0 to 5;

P is 0 to 4;

W is selected from halogen, CN, $NO_2$, $C_1$ to $C_2$ alkyl, $C_1$ to $C_2$ haloalkyl, $C_1$ to $C_2$ alkoxy, $C_1$-$C_2$ haloalkoxy, $C_1$ to $C_2$ alkylthio, $C_1$ to $C_2$ haloalkylthio, $C_1$ to $C_2$ alkylsulfonyl and $C_1$ to $C_2$ haloalkylsulfonyl;

X is O or S; and

Y is selected from H, $C_1$ to $C_6$ alkyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, and phenylthio substituted with 1 to 3 substituents independently selected from W.

2. A compound according to claim 1 wherein:

$R_6$ is H;

$R_7$ is H;

n and p are independently 0 to 2; and m is 1 to 2.

3. A compound according to claim 2 wherein:

$R_1$, $R_2$, and $R_3$ are independently $R_8$, halogen, CN, $NO_2$, $OR_8$, $SR_8$, $S(O)R_8$, $S(O)_2R_8$ or $NR_8R_9$, or when m, n or p is 2, $R_1$, $R_2$ or $R_3$ can be taken together as $OCH_2O$, $OCH_2CH_2O$ or $CH_2CH_2O$, each of which can be substituted with 1 to 4 halogen atoms or 1 to 2 methyl groups;

$R_8$ is $C_1$ to $C_2$ alkyl, $C_3$ to $C_4$ alkenyl, $C_1$ to $C_2$ haloalkyl, $C_3$ to $C_4$ haloalkenyl or phenyl optionally substituted with halogen;

$R_9$ is H or $C_1$ to $C_2$ alkyl; and

X is O.

4. A compound according to claim 3 wherein:

$R_1$ is halogen, CN, $NO_2$, $OCF_2H$, $OCF_3$ $OCF_2CF_2H$, $CF_3$ or when m is 2 then $R_1$ may be taken together as $CH_2C(CH_3)_2O$ or $CF_2CF_2O$ to form a 5 membered ring.

$R_2$ is H, halogen, CN, $NO_2$, $OCH_3$, $OCF_2H$, $OCR_3$, $SCH_3$, $SCF_2H$, $SCR_3$, $CR_3$, $OCF_2CF_2H$ or phenoxy;

$R_3$ is halogen;

$R_5$ is $C(O)OR_{10}$, $C(O)R_{10}$, $C(O)NR_{10}R_{11}$ or $S(O)_2NR_{10}R_{11}$;

$R_{10}$ is H, $C_1$ to $C_4$ alkyl, $C_3$ to $C_4$ alkenyl, $C_3$ to $C_4$ alkynyl, $C_1$ to $C_4$ haloalkyl, $C_3$ to $C_4$ haloalkenyl, $C_1$ to $C_4$ alkyl substituted with CN, $C(O)OCH_3$, $C(O)OCH_2CH_3$, $OCH_3$, $OCH_2CH_3$, $SCH_3$, $SCH_2CH_3$ and $NO_2$;

$R_{11}$ is H or $C_1$ to $C_2$ alkyl; and

Y is H, $C_1$ to $C_6$ alkyl, CHO, $C_2$ to $C_6$ alkylcarbonyl or $C_2$ to $C_6$ alkoxycarbonyl.

5. A compound according to claim 4 wherein:
$R_5$ is $C(O)OR_{10}$;
$R_{10}$ is $C_1$ to $C_3$ alkyl, $C_2$ to $C_3$ haloalkyl, propargyl or allyl; and one of $R_3$ or $R_5$ is in the para-position and one of $R_1$ is in the para-position; and
Y is H, $CH_3$ $C(O)CH_3$, $C(O)OCH_3$ or CHO.

6. A compound according to claim 5 which is:
methyl 4-[3-(4-chlorophenyl)-4,5-dihydro-1-[[4-(trifluoromethyl)phenylamino]carbonyl]-1H-pyrazol-4-yl]benzoate.

7. A compound according to claim 5 which is:
methyl 4-[3-(4-chlorophenyl)-1-[(4-chlorophenyl)aminocarbonyl]-4,5-dihydro-1H-pyrazol-4-yl]benzoate.

8. A compound according to claim 5 which is:
methyl 4-[3-(4-fluorophenyl)-4,5-dihydro-1-[[4-(trifluoromethyl)phenylamino]carbonyl]-1H-pyrazol-4-yl]benzoate.

9. A compound according to claim 5 which is:
methyl 4-[1-(4-chlorophenyl)aminocarbonyl]-[3-(4-fluorophenyl)-4,5-dihydro-1H-pyrazol-4-yl]benzoate.

10. A compound according to claim 5 which is:
ethyl 4-[3-(4-chlorophenyl)-4,5-dihydro-1-[[4-(trifluoromethyl)phenylamino]carbonyl]-1H-pyrazol-4-yl]benzoate.

11. A compound according to claim 5 which is:
ethyl 4-[1-[(4-bromophenyl)aminocarbonyl]-3-(4-chlorophenyl)-4,5-dihydro-1H-pyrazol-4-yl]benzoate.

12. A compound according to claim 5 which is:
methyl, 4-[3-(4-bromophenyl)-4,5-dihydro-1-[[4-(trifluoromethyl)phenylamino]carbonyl]-1H-pyrazol-4-yl]benzoate.

13. A compound according to claim 5 which is:
methyl 4-[3-(4-cyanophenyl)-4,5-dihydro-1-[[4-(trifluoromethyl)phenylamino]carbonyl]-1H-pyrazol-4-yl]benzoate.

14. A composition comprising an insecticidally effective amount of a compound according to any one of claims 1 to 13 together with a carrier therefor.

15. A method for controlling insects comprising applying to the insect or its environment an insecticidally effective amount of a compound according to any one of claims 1 to 13.

* * * * *